United States Patent
Saker et al.

(10) Patent No.: US 6,840,952 B2
(45) Date of Patent: Jan. 11, 2005

(54) TISSUE TRACT SEALING DEVICE

(75) Inventors: Mark B. Saker, c/o Vascular Solutions, Inc., 2495 Xenium La., Minneapolis, MN (US) 55441; James V. Kauphusman, Champlin, MN (US)

(73) Assignee: Mark B. Saker, Chicago, IL (US)

( * ) Notice: Subject to any disclaimer, the term of this patent is extended or adjusted under 35 U.S.C. 154(b) by 0 days.

(21) Appl. No.: 10/007,786

(22) Filed: Dec. 7, 2001

(65) Prior Publication Data

US 2002/0091411 A1 Jul. 11, 2002

Related U.S. Application Data

(60) Provisional application No. 60/251,912, filed on Dec. 7, 2000.

(51) Int. Cl.$^7$ .............................................. A61B 17/08
(52) U.S. Cl. ...................... 606/213; 606/215; 604/264; 604/235; 604/187
(58) Field of Search ........................ 222/387; 606/213, 606/214, 215, 92–95; 604/158, 164.01, 164.02, 264, 235, 232, 231, 187, 193, 200, 218, 181, 214, 221, 240; D24/113

(56) References Cited

U.S. PATENT DOCUMENTS

| | | | | |
|---|---|---|---|---|
| 3,604,595 A | * | 9/1971 | Wiedeman ................. | 222/99 |
| 3,906,947 A | * | 9/1975 | Cloyd ...................... | 604/231 |
| 4,452,823 A | * | 6/1984 | Connolly et al. .......... | 426/115 |
| 5,116,319 A | * | 5/1992 | van den Haak ............ | 604/110 |
| 5,383,864 A | * | 1/1995 | van den Heuvel ......... | 604/218 |
| 5,413,564 A | * | 5/1995 | Silver et al. ............... | 604/232 |
| 5,522,812 A | * | 6/1996 | Talonn et al. .............. | 604/198 |
| 5,746,215 A | * | 5/1998 | Manjarrez .................. | 600/573 |
| 6,071,301 A | | 6/2000 | Cragg et al. ............... | 606/213 |
| 6,086,607 A | | 7/2000 | Cragg et al. ............... | 606/213 |
| 6,096,005 A | * | 8/2000 | Botich et al. .............. | 604/110 |
| 6,200,328 B1 | | 3/2001 | Cragg et al. ............... | 606/213 |
| 6,248,094 B1 | * | 6/2001 | Epperson .................. | 604/195 |

OTHER PUBLICATIONS

D. Ayar et al., *Needle–track metastasis after transthoracic needle biopsy*, Abstract, Department of Radiology, University of Alabama at Birmingham.

F. Navarro et al., *Diaphragmatic and subcutaneous seeding of hepatocellular carcinoma following fine–needle aspiration biopsy*, Abstract, Department de Transplantation Hepatique, Service de Chirurgie Digestive C, Montepellier, France.

Erik K. Paulson, MD et al., *Use of Fibrin Sealant as a Hemostatic Agent after Liver Biopsy in Swin*[1], JVIR, Jul.–Aug. 2000, pp 905–911.

Erich K. Lane, MD et al., *Autologous Blood Clot Seal to Prevent Pneumothorax at CT–guided Lung Biopsy*[1], Radiology, Jul. 2000, pp 93–96.

Theodore Petsas et al., *Fibrin Glue for Sealing the Needle Track After Percutaneous Lung Biopsy: Part I—Experimental Study*, Cardio Vascular and Interventional Radiology, 1995, pp 372–377.

(List continued on next page.)

Primary Examiner—David O. Reip
Assistant Examiner—D. Jacob Davis
(74) Attorney, Agent, or Firm—Patterson, Thuente, Skaar Christensen, P.A.

(57) ABSTRACT

A device and system for delivery of a flowable biocompatible material to a tissue tract in a controlled manner generally includes a reservoir adapted to be in fluid connection with a cannula, a discharging mechanism adapted to discharge the contents of the reservoir and a cannula retractor to withdraw the cannula. The cannula retractor is operably interconnected with the discharging mechanism so that a measured quantity of the reservoir contents is smoothly discharged to substantially fill at least a portion of the tissue tract.

6 Claims, 19 Drawing Sheets

OTHER PUBLICATIONS

Theodore Petsas et al., *Fibrin Glue for Sealing the Needle Track After Percutaneous Lung Biopsy: Part II—Clinical Study*, Cardio Vascular and Interventional Radiology, 1995, pp 378–382.

Christopher E. Engler, MD et al., *Pneumothorax after Lung Biopsy: Prevention with Transpleural Placement of Compressed Collagen Foam Plugs*[1], Radiology, Sep. 1992, pp 787–789.

Ronald McCartney, MD et al., *A Technique for the Prevention of Pneumothorax in Pulmonary Aspiration Biopsy*, Loma Linda University, Sep. 1973, pp 872–875.

Vincent P. Chuang, MD et al., *Sheath Needle for Liver Biopsy in High–Risk Patients*[1], Radiology, Jan. 1988, pp 261–262.

Marc Zins, MD et al., *US–guided Percutaneous Liver Biopsy with Plugging of the Needle Track: A Propective Study in 72 High–Risk Patients*[1], Radiology, Sep. 1992, pp 841–843.

Judith L. Chezmar, MD et al., *Liver Transplant Biopsies with a Biopsy Gun*[1], Radiology, May 1991, pp 447–448.

Andrew F. Little et al., *Transjugular Liver Biopsy: A Prospective Study in 43 Patients with the Quick–Core Biopsy Needle*[1], JVIR, Jan.–Feb. 1996, pp 127–131.

Joseph E. Cox, MD et al., *Transthoracic Needle Aspiration Biopsy: Variables That Affect Risk of Pneumothorax*[1], Radiology, Jul. 1999, pp165–168.

V.G. McDermott, MD et al., *Transhepatic Liver Biopsy with Tract Embolization*, Scientific Session 19: Liver—Interventional, p. 109.

* cited by examiner

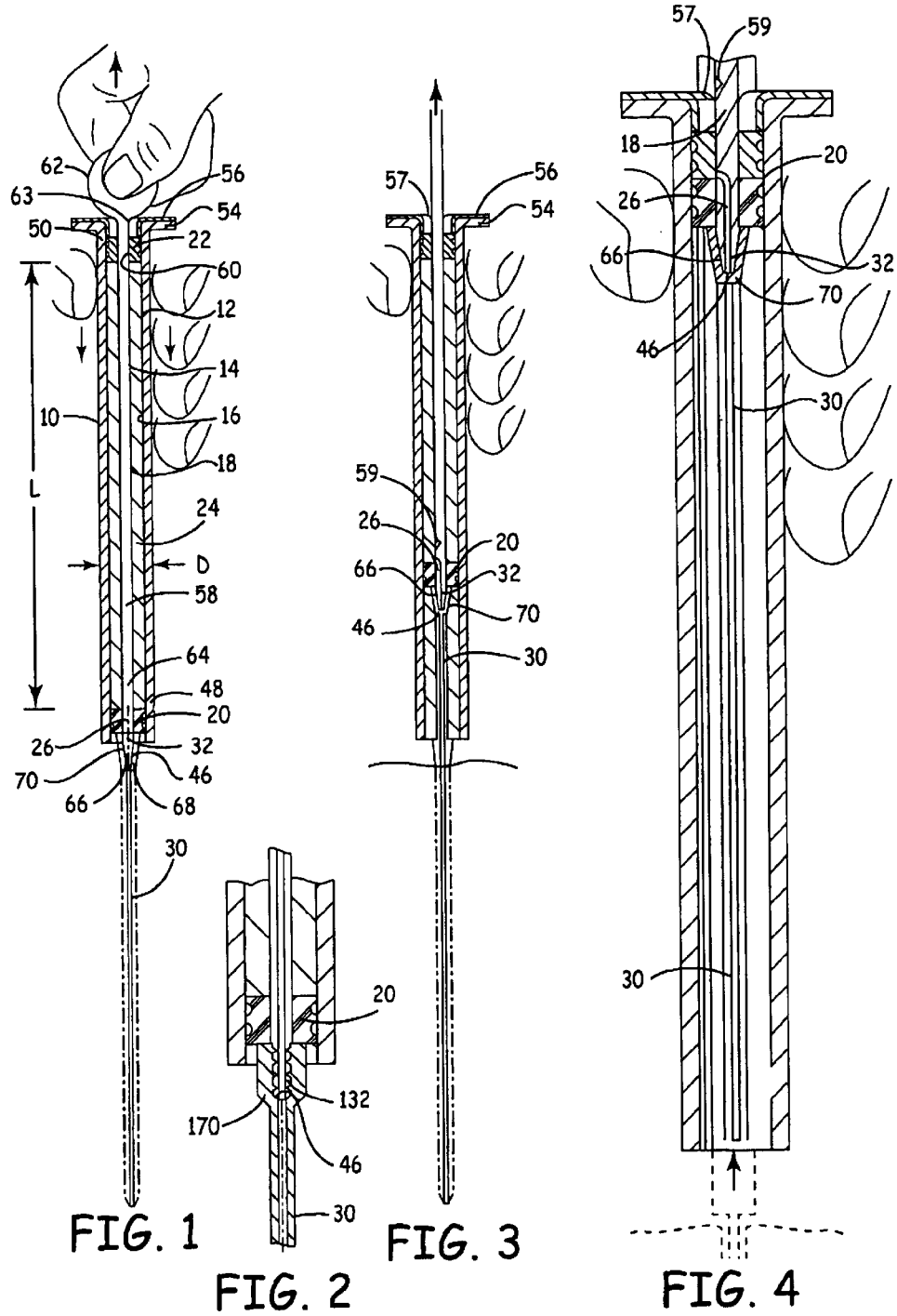

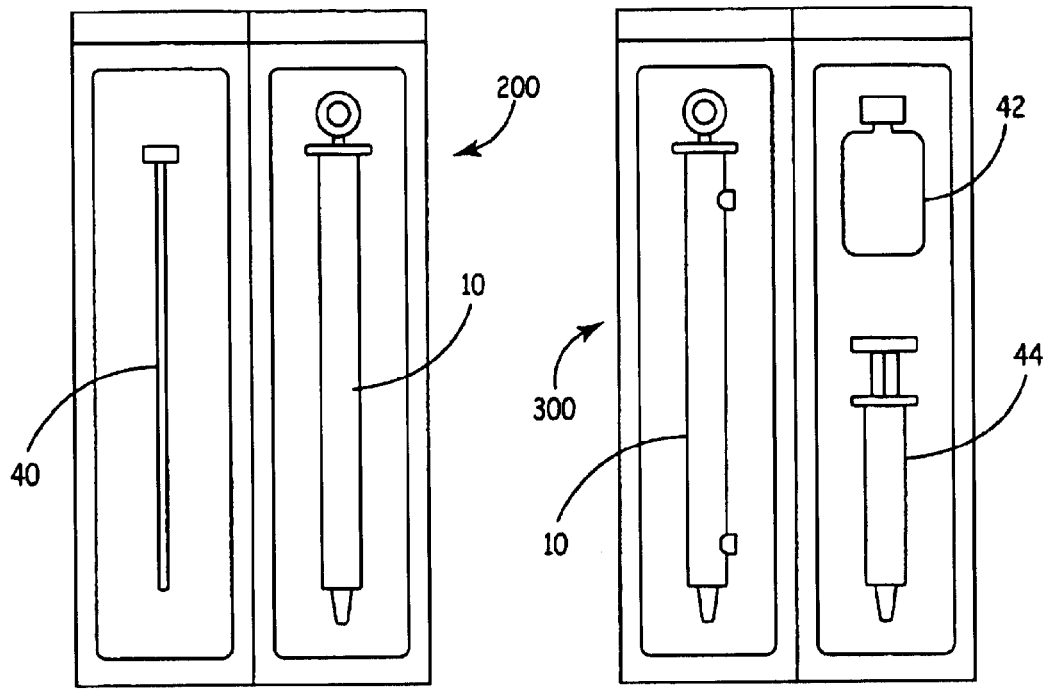
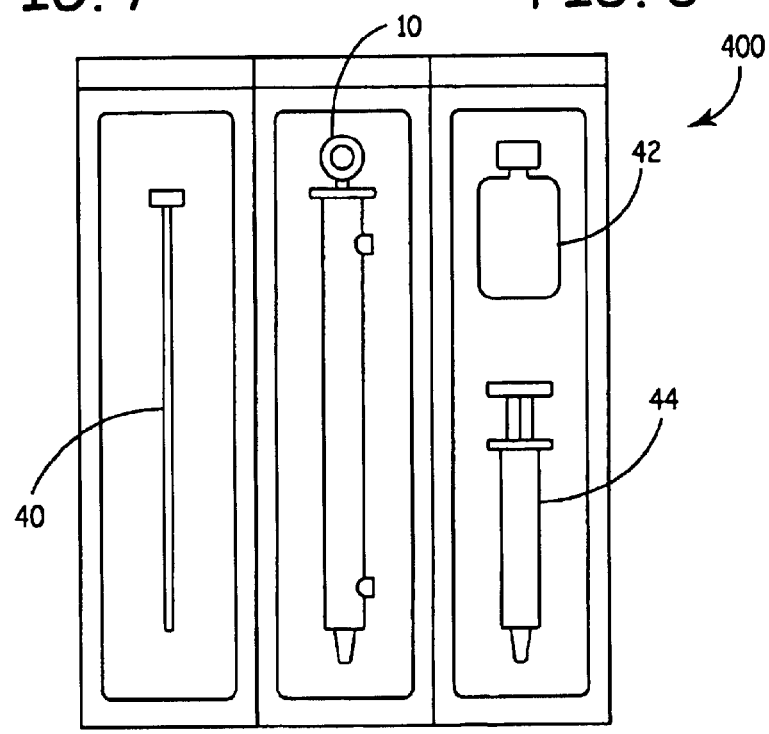
FIG. 7  FIG. 8
FIG. 9

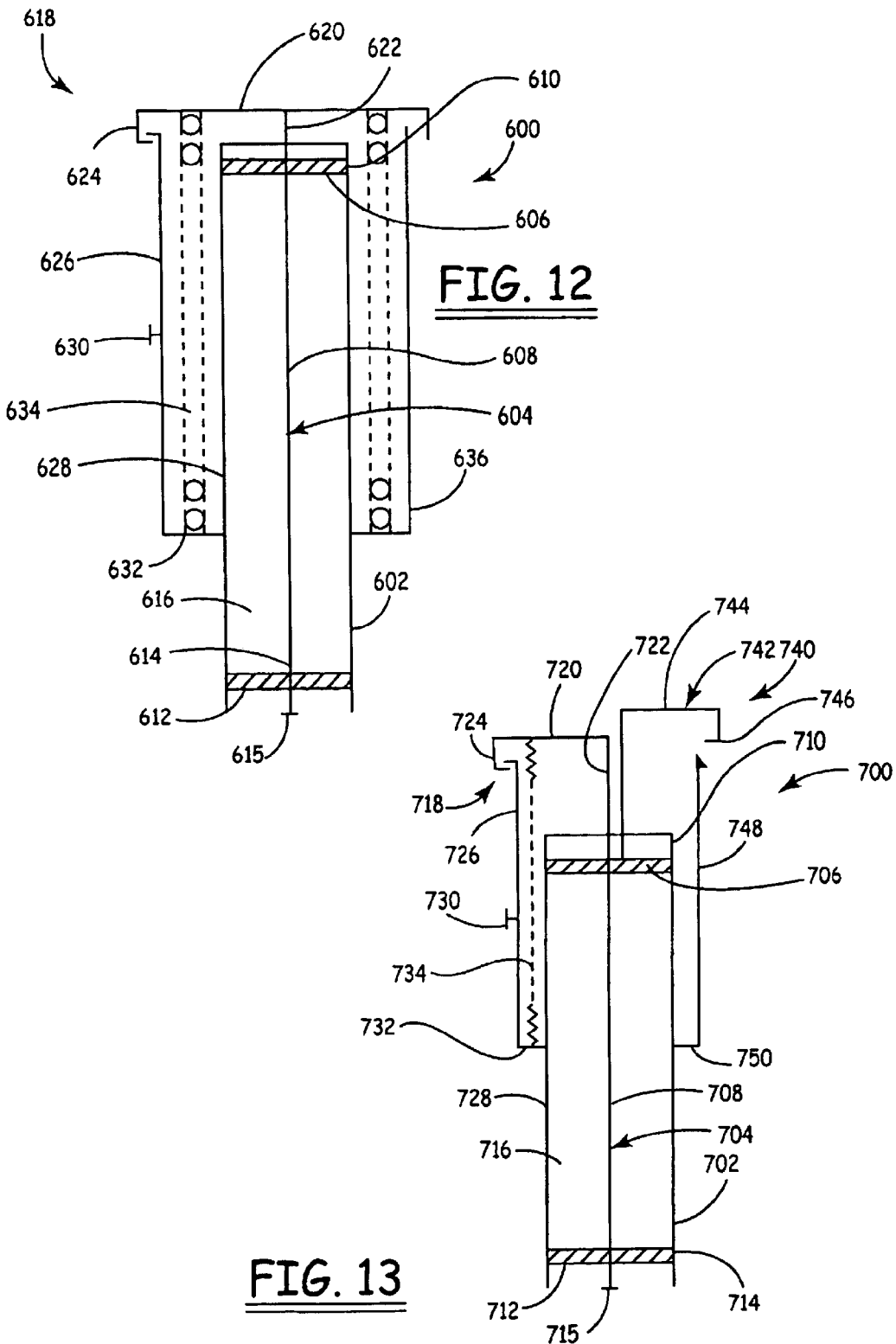

TISSUE TRACT SEALING DEVICE

RELATED APPLICATION

The present application claims priority to U.S. Provisional Application No. 60/251,912, filed Dec. 7, 2000, entitled "TISSUE TRACK SEALING DEVICE." The identified provisional patent application is hereby incorporated by reference in its entirety.

FIELD OF INVENTION

This invention relates generally to medical devices used in needle biopsies. More particularly it relates to closing the tissue tract left after a needle biopsy.

BACKGROUND OF THE INVENTION

Many medical procedures require the insertion of a tube-like member, such as a catheter, sheath, or other tube to gain access through tissue and guide other instruments to the procedure site. After completion of the procedure, the tube-like member is removed from the patient generating a tissue tract in its path of withdrawal.

One such medical procedure is a needle biopsy performed more than one-half million times in the United States each year. Typically, access for the biopsy is provided by a guiding cannula (such as an 18-gauge sheath) through which a biopsy needle (such as a 19-gauge cutting needle) is advanced to the tissue biopsy site. The tissue biopsy is harvested and the cutting needle is withdrawn from the guiding cannula. The guiding cannula is maintained at the biopsy site until it is determined whether or not an additional sample is required (resulting in the reinsertion of the needle). If no further sampling is necessary, the guiding cannula is withdrawn. In every needle biopsy, the patient has a propensity to encounter complications due to bleeding at the location where the biopsy was taken and in the tissue tract caused by the removal of the tube-like member. Malignancy of the tissue at the biopsy site may further increase this propensity. See Marc Zins, et al., "US-Guided Percutaneous Liver Biopsy with Plugging of the Needle Tract: A Prospective Study in 72 High-risk Patients," *Radiology*, 184:841, 843 (1992). This propensity for bleeding can be minimized by depositing an appropriate hemostatic material that will embolize the biopsy site and tissue tract by stimulating the coagulation of blood after the biopsy needle has been withdrawn. Devices currently available deposit the hemostatic material by attaching a loaded syringe to the tube-like member that is still inside the tissue. Material is injected into the tube-like member with one hand, via the syringe, while the other hand manually withdraws the sheath from the patient.

Guiding cannula provide access to enable biopsies of most organs. Lung biopsies are complicated most often by pneumothorax, or the leaking of air or gas into the membrane lining the lungs, necessitating a chest tube and an extended hospital stay. Thus, it is desirable to prevent pneumothorax by sealing the tissue tract after the biopsy. This has been successfully accomplished by delivering autologous blood clot material prepared from a 4–8 mL aliquot of the patient's blood (which was given time to clot) and 0.5–1.5 mL of supernatant. This material is injected into the tissue tract through the tube-like member as the tube-like member is being removed from the patient. See Erich K. Lang, et al., "Autologous Blood Clot Seal to Prevent Pneumothorax at CT-Guided Lung Biopsy," *Radiology*, 216:93, 94 (2000).

There are several hemostatic materials, such as procoagulants or sealants, which have been employed in needle biopsies. While differing in name and percent composition, these materials have a common ability to facilitate the clotting of blood. For example, fibrin sealant, such as that manufactured by Baxter Healthcare Corp., Glendale, Calif., under the name Tisseel®, is composed of fibrinogen and thrombin (1000 U derived from human pooled plasma). Before use, the thrombin must be re-hydrated and suspended in 40 gmol/mL of calcium chloride solution (2-mL vial). The fibrinogen is re-hydrated in a fibrinolysis inhibitor solution of 3000 inactivator units of aprotin. These two solutions are loaded into two identical 2-mL syringes attached via a plastic clip to a common plunger that is connected to the sheath. See Erik K. Paulson, et al., "Use of Fibrin Sealant as a Haemostatic Agent after Liver Biopsy in Swine," *JVIR*, 11:905–911 (2000).

A similar example of hemostatic material is fibrin glue, such as that sold under the name Tissucol® by Immuno AG, Vienna, Austria. Tissucol® is a protein-based sealer of human plasma containing 500 IU of thrombin and 0.1 mL 1131 fibrinogen, from CIS Bio International, Gif-Sur-Yvette, France, and 0.2 mL of contrast medium to tract its progression called Omnipaque 300™, from Schering AG, Berlin, Germany. The delivery mechanism of the fibrin glue is similar to that of the other materials. The glue is loaded into a syringe that dispenses the material in aliquots followed by manually removing the tube-like member as the material is being dispersed.

GelFoam® is another hemostatic product, manufactured by Pharmacia & Upjohn of Kalamazoo, Mich. GelFoam® is composed of gelatinous porcine, which is primarily collagen. Prior to use, the GelFoam® is hydrated, cut into a desired size (such as 5×5×20-mm pieces), and placed one by one, into the tip of a 1-mL tuberculin syringe. Contrast medium may then be added to the syringe. GelFoam® is injected into the tube-like member with the help of a fluoroscope. After each piece is delivered, the syringe and the tube-like member are withdrawn approximately 2-cm and another pre-cut piece of GelFoam™ is injected. This process of injection followed by withdrawal is repeated until the tissue tract is sealed. See, Vincent P Chuang, et al., Sheath Needle for Liver Biopsy in High-risk Patients, *Radiology*, 166:261–262 (1988).

A biopsy is frequently required in order to obtain a sample of a tumor or other malignant tissue from a patient. A concern of the oncologist is the transmission of tumor cells from the biopsy site during the withdrawal of the guiding cannula that provided access into the tumor. This so-called "needle tract seeding" is a complication that may occur in as many as one in every 1000 procedures. In cases such as these, it is desirable to deposit some form of material, perhaps combined with an anticoagulant, throughout the tissue tract to promote clotting and to minimize the potential seeding of cancer cells in nearby tissue.

Regardless of the medical procedure, the delivery mechanisms currently available all operate by injecting the hemostatic material with one hand and manually withdrawing the tube-like member from the patient with the other hand. Existing devices and their required delivery mechanism provide limited accuracy with respect to the amount of material deposited, and limited control and precision with respect to the location of delivery of material in the tissue tract. The need for dosage control is especially acute when the hemostatic material contains thrombin due to the threat of thrombosis.

There is a need to provide an apparatus capable of controllably delivering an accurate amount of hemostatic material precisely along a tissue tract.

SUMMARY OF THE INVENTION

The present invention is a device and system for delivery of a flowable biocompatible material to a tissue tract in a controlled manner. The instrument of the present invention generally includes a reservoir adapted to be in fluid connection with a cannula, a discharging mechanism adapted to discharge the contents of the reservoir, and a cannula retractor to withdraw the cannula. The cannula retractor is operably interconnected with the discharging mechanism so that a measured quantity of the reservoir contents is smoothly discharged to substantially fill at least a portion of the tissue tract.

In some embodiments, the invention includes a primer adapted to prefill the cannula with a sufficient quantity of flowable biocompatible material so that the material begins to discharge as soon as the cannula is withdrawn. The discharging mechanism may include a piston and cylinder or a compressible flexible reservoir.

The present invention overcomes the disadvantages of the existing techniques for manually sealing tissue tracts and fills the need for an apparatus capable of controllably delivering an accurate amount of hemostatic material precisely along a tissue tract.

BRIEF DESCRIPTION OF THE DRAWINGS

FIG. 1 is a cross-section view of an apparatus in accordance with a preferred embodiment of the invention.

FIG. 2 is a cross-section view of the apparatus attached to a hub adapted for connecting a tube-like member in accordance with a preferred embodiment of the invention.

FIG. 3 is a cross-section view of a cylindrical housing of the apparatus, the hub, and the tube-like member in a state of partial uptake into the cylindrical housing of the apparatus.

FIG. 4 is a cross-section view of the apparatus, the hub, and the tube-like member in a state of complete uptake into a cylindrical housing of the apparatus.

FIG. 7 is a kit containing an apparatus preloaded with a material and a needle in accordance with a preferred embodiment.

FIG. 8 is a kit containing an apparatus with an external side-port, an ampoule of a material and a syringe for loading the apparatus in accordance with another preferred embodiment.

FIG. 9 is a kit containing the apparatus with the external side-port, the ampoule of the material, the syringe for loading the apparatus, and a needle in accordance with another preferred embodiment.

FIG. 12 is a schematic representation of an automatically operating apparatus according to a preferred embodiment of the invention.

FIG. 13 is a schematic representation of an automatically operating apparatus according to another preferred embodiment of the invention in a first configuration.

DETAILED DESCRIPTION OF THE PREFERRED EMBODIMENTS

Tissue tracts are generated in numerous medical procedures upon the removal of a tube-like member from the patient. The procedure described herein in connection with the preferred embodiments of the invention is a biopsy, but the apparatus, methods, and kits according to the invention are not limited to use in biopsy procedures. In addition, the invention is described in terms of sealing a tissue tract formed by a guiding cannula used during a needle biopsy. It will be appreciated that the invention has application beyond the sealing of a tissue tract formed by a guiding cannula, and in fact, the invention has application to the sealing of virtually any tract formed by a tube-like member, such as a cannula, a sheath, a catheter and the like.

A biopsy procedure begins by advancing a guiding cannula to the tissue biopsy site. A sampling needle or sample-taking tool is then inserted through the guiding cannula to the biopsy site, and a tissue sample is harvested and withdrawn from the site through the cannula. While in place, the cannula defines a tract within the tissue (referred to herein as a tissue tract), and the apparatus and method of this invention may be employed to seal the tissue tract while concomitantly withdrawing the sheath from the patient.

Figure 5:
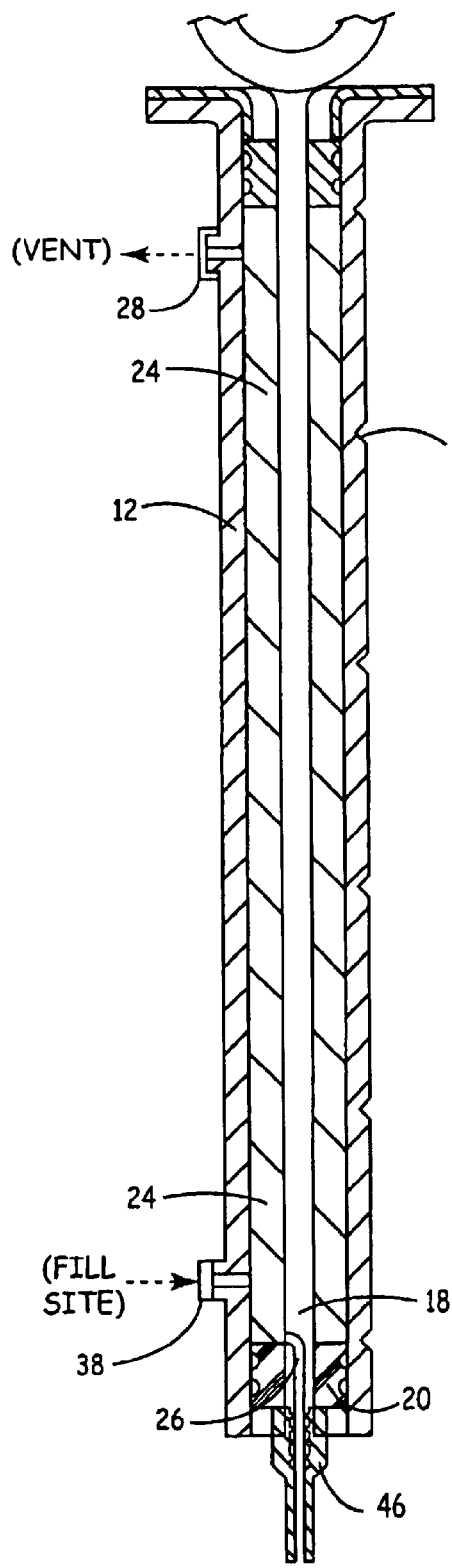
FIG. 5 is a cross-section view of the apparatus featuring an external side-port and a vent-port.

An apparatus 10 in accordance with a first preferred embodiment of the invention, as shown in FIG. 1, includes a cylindrical housing 12 that is made preferably from a transparent plastic. The housing 12 has an outer surface 14 and an inner surface 16, and maybe formed with graduations 30, as shown in FIG. 5, marked on the outer surface 14. The inner surface 16 extends an entire length of the cylindrical housing 12 from a distal end 48 and a proximate end 50 thereof. A flange 54 is formed integral with the proximate end 50. One of ordinary skill in the art will appreciate the similarities between the cylindrical housing and a syringe body and will readily appreciate that the cylindrical housing 12 may be adapted from a syringe body using customary design techniques. Additionally, while illustrated as a right circular cylinder, the cylindrical housing 12 need not be so configured and may have various cross-sectional configurations such as, without limitation, elliptical, rectangular, triangular, and combinations thereof. A seal 22 is disposed within the cylindrical housing 12 at the proximate end 50. An end cap 56 is provided for retaining the seal 22 within the cylindrical housing. It is possible to otherwise retain the seal 22 at the proximate end 50 other than with the end cap 56 such as by, for example, forming the proximate end 50 with a recess to receive the seal 22. Additionally, the seal 22 may be formed integrally with the end cap 56. As will be appreciated from the description of the additional preferred embodiments of the invention, the end cap 56 may be also arranged for distal translation relative to the cylindrical housing 12 for advancing the seal 22 distally within the cylindrical housing 12.

The apparatus 10 also includes a plunger 18 that is disposed within the cylindrical housing 12. The plunger 18 includes a shaft 58 that is slidably received within an aperture 60 formed within the seal 22. Separated by the shaft 58 are a grip 62 formed at a proximate end 63 of the plunger 18 and a hub 32 formed at a distal end 64 of the plunger 18.

The end cap 56 may be further formed with a tab 57 that, as best seen in FIG. 3, rests against the plunger 18. Near the distal end 48, the shaft 58 is formed with a notch 59. As illustrated in FIG. 4, when the plunger 18 is in a fully withdrawn position, the tab 57 engages the notch 59 to prohibit the plunger from being advanced back into the cylindrical housing 12. Additionally, as illustrated in FIG. 4, the cylindrical housing 12 is sized to a length such that the withdrawn cannula 30 remains entirely within the confines of the cylindrical housing 12. Provided by this arrangement of the cylindrical housing 12, the tab 57 and the notch 59 is a safe disposal configuration for the apparatus and cannula 30 following use.

As shown in FIG. 1, the hub 32 includes a partial tapered cone 66 for engaging a compatible recess 68 formed in a receiver portion 70 of a cannula 30 for securing the plunger 18 to the cannula 30. The hub 32 may alternatively be formed as a luer fitting 132, with the receiver portion 170 being suitably adapted to be compatible with such a fitting for attaching the plunger 18 to the cannula 30, as shown in FIG. 2.

A seal 20 is also disposed within the cylindrical housing 12 at the distal end 48. The seal 20 is adapted for movement with the distal end 64 of the plunger 18, and as shown in FIG. 1, the seal 20 is received about and retained to the shaft 58 adjacent the hub 32. For example, the seal 20 may be received within a recess (not shown) formed in the shaft 58.

A volume 24 is defined by the inner surface 16 of the cylindrical housing 12, the shaft 58, the first seal 20 and the second seal 22. To place the volume 24 into communication with the passage of the cannula 30, a chamber 26 is formed in the shaft 58 and extending through the hub 32, exiting the hub 32 through an aperture 46.

The volume 24 may contain a material 42, such as a hemostatic material. Material 42 is a flowable biocompatible material. Material 42 is flowable in that material 42 has a capacity to move with a continued change of place among the constituent particles that constitute the material. Examples of flowable material 42 include: liquids, gels, foams, suspensions, powders, or granular materials, or any combination thereof. Flowable material 42 is biocompatible in the sense that in general the material does not cause an antigen-antibody response when introduced into a living creature. The material 42 can be either preloaded into the volume 24 or loaded into the volume 24 via a syringe 44 injecting into an external side-port 38 which communicates with the volume 24, as shown in FIG. 5. In such an arrangement the apparatus 10, a vent-port 28 may be provided for evacuating air from the volume 24 as the material is injected into the chamber 24 via the side-port 38. The material generally may be any therapeutic material, such as various types of procoagulant materials described herein and/or chemotherapeutic materials. Examples of materials 42 suitable for use with the present invention include: hemostatic materials, procoagulant, fibrin, fibrinogen, thrombin, collagen, a cancer chemotherapeutic agent, cynoacrylate, cross-linking polymer, hydrogel, photo-initiated adhesives, autologous blood or any combination thereof.

To use the apparatus 10, and upon completion of the medical procedure requiring the placement of the cannula 30 within the tissue of a patient, a medical professional secures the apparatus 10 to the cannula 30 by engaging the hub 32 with the receiver portion 70. Next, grasping with one hand the distal end 48 of the cylindrical housing 12, the plunger 18 is translated proximately from the cylindrical housing 12 by grasping and applying a withdrawing force to the grip 62. The proximate translation of the plunger 18 draws the seal 20 towards the seal 22, thereby decreasing the volume 24. The hemostatic material, being substantially incompressible, is expelled from the volume 24 through the chamber 26 and aperture 46 into the cannula 30. Concomitantly, the cannula 30 is withdrawn from the tissue and into the cylindrical housing 12, as shown progressively in FIGS. 3 and 4. The diameter of the inner surface 16 of the cylindrical housing 12 is sized sufficiently to receive the hub 32 and the cannula 30. The graduations 30 facilitate the accurate dispensing of the material 42 as the entirety of the cannula 30 is taken up into the cylindrical housing 12, as shown in FIG. 4. It is appreciated that this pinning of the apparatus 10 and the pulling of plunger 18 to dispense the material 42 while concomitantly withdrawing the cannula 30 addresses a need in the art to controllably dispense a precise amount of material into a tissue tract. For example, the volume 24 may be sized such that a one-to-one relationship exists between the volume of material displaced as the plunger 18 is withdrawn to the volume of the tissue tract evacuated by the cannula 30.

Figure 6:
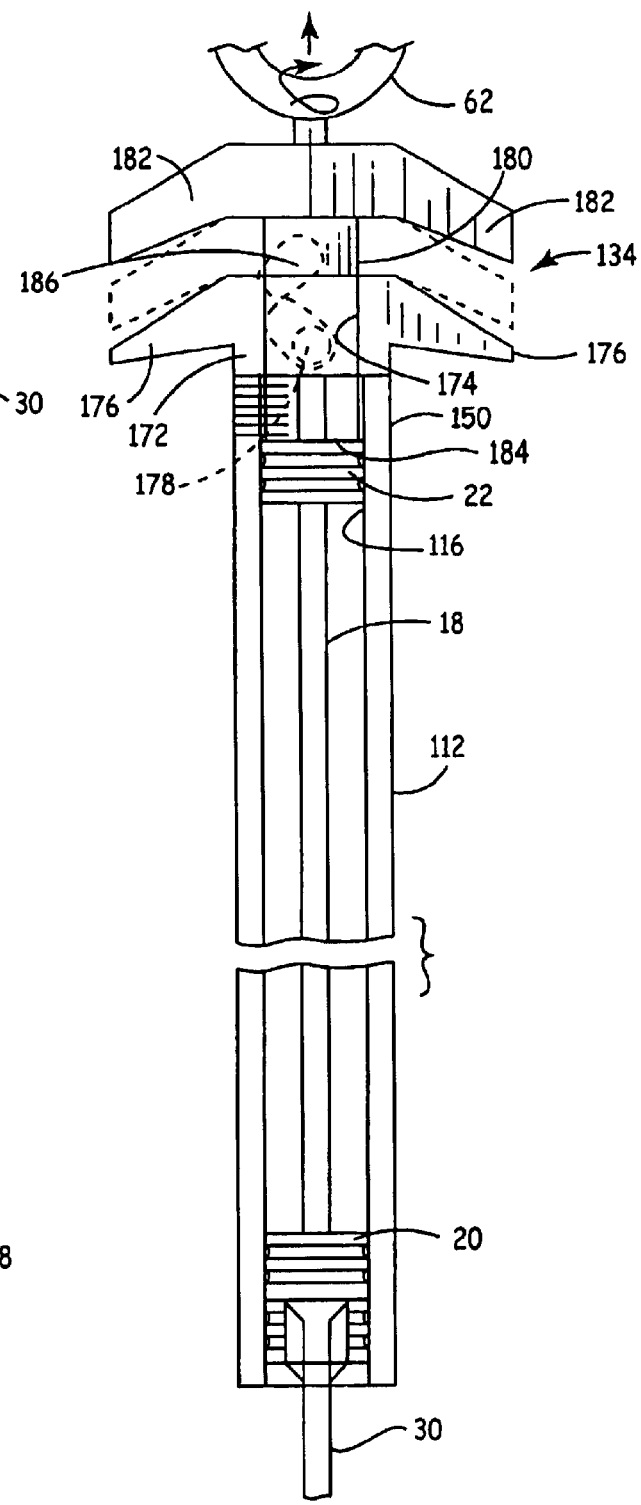
FIG. 6 is a cross-section view of an apparatus in accordance with another preferred embodiment of the invention featuring a second plunger and a locking mechanism.

In another embodiment of the invention illustrated by the apparatus 100 shown in FIG. 6., wherein like reference numerals refer to like elements from the preceding embodiments, there is a plunger 134 slidably received within the cylindrical housing 112 and adapted to displace the seal 22. When the plunger 34 is depressed distally towards the cylindrical housing 12, the seal 22 is propelled distally towards the seal 20 decreasing the volume 24 such that the material 42 in the volume 24 communicates through the chamber 26 and aperture 46 into the cannula 30. This action primes the cannula 30 with material prior to withdrawal of the cannula 30 from the tissue tract. After the cannula 30 is primed, the pinning and pulling procedure for withdrawing the cannula 30 and for depositing the material 42 in the tissue tract proceeds as described above.

More particularly, the plunger 134 may contain a locking mechanism such as the cam and a follower arrangement shown in FIG. 6. The distal end 150 of the cylindrical housing 112 is formed to include a cam base 172. The cam base 172 includes a cylindrical surface 174 formed through the cam base 172 that is aligned with the inner surface 116 of the cylindrical housing, and a pair of radially outwardly extending tabs 176. Formed on the inner surface 116 is a cam follower (illustrated in phantom as cam follower 178 in FIG. 6). The plunger 134 includes a cylindrical portion 180 that extends into the cylindrical surface 174 and includes an end surface 184 that engages the seal 22. The plunger 134 also includes a pair of radially outwardly extending tabs 182. The cylindrical portion 180 is formed with a cam surface 186 into which the cam follower 178 is received. By grasping in one hand the tabs 176 and applying rotating torque to the tabs 182, the second plunger 134 is caused to rotate with respect to the cylindrical housing 112. Action of the cam follower 178 engaging the cam surface 186 causes a distal translation of the plunger 134 into the cylindrical housing 112. The distal translation of the plunger 134 causes distal displacement of the seal 22 towards the seal 20 thereby decreasing the volume 24. Locking mechanisms other than the cam and follower arrangement described herein, such as ratchet and pawl, dog and catch, and the like may be used.

The locking mechanism may control depression of the plunger 134 distally to facilitate the controlled priming of the cannula 30 with material, as described above, prior to its withdrawal from the patient. Upon completion of the depression of the plunger 134, the locking mechanism (cam follower 178 and cam surface 186) secures the plunger 134 and hence the seal 22 from movement within the cylindrical housing 112 to enable the pin and pull procedure for withdrawing the cannula 30 and depositing the material 42 in the tissue tract.

Another preferred embodiment of the invention is a kit 200 containing the apparatus 10, in any of the preloaded embodiments described herein, and a needle contained in a tube-like member, collectively system 40, such as those used to perform biopsies, or a similar device in the event of another procedure. The kit 200, as shown in FIG. 7, would be useful in an operation suite where all the sterilized equipment to perform the biopsy and to seal the needle tract is provided in one package.

Another kit 300 is shown in FIG. 8. The kit 300 would be applicable with an apparatus 10 that requires the loading of material 42 via injection from a syringe 44 into the external side-port 38. This kit may also include the system 40 necessary to perform the desired medical procedure, as represented by kit 400 in FIG. 9.

Figure 10:
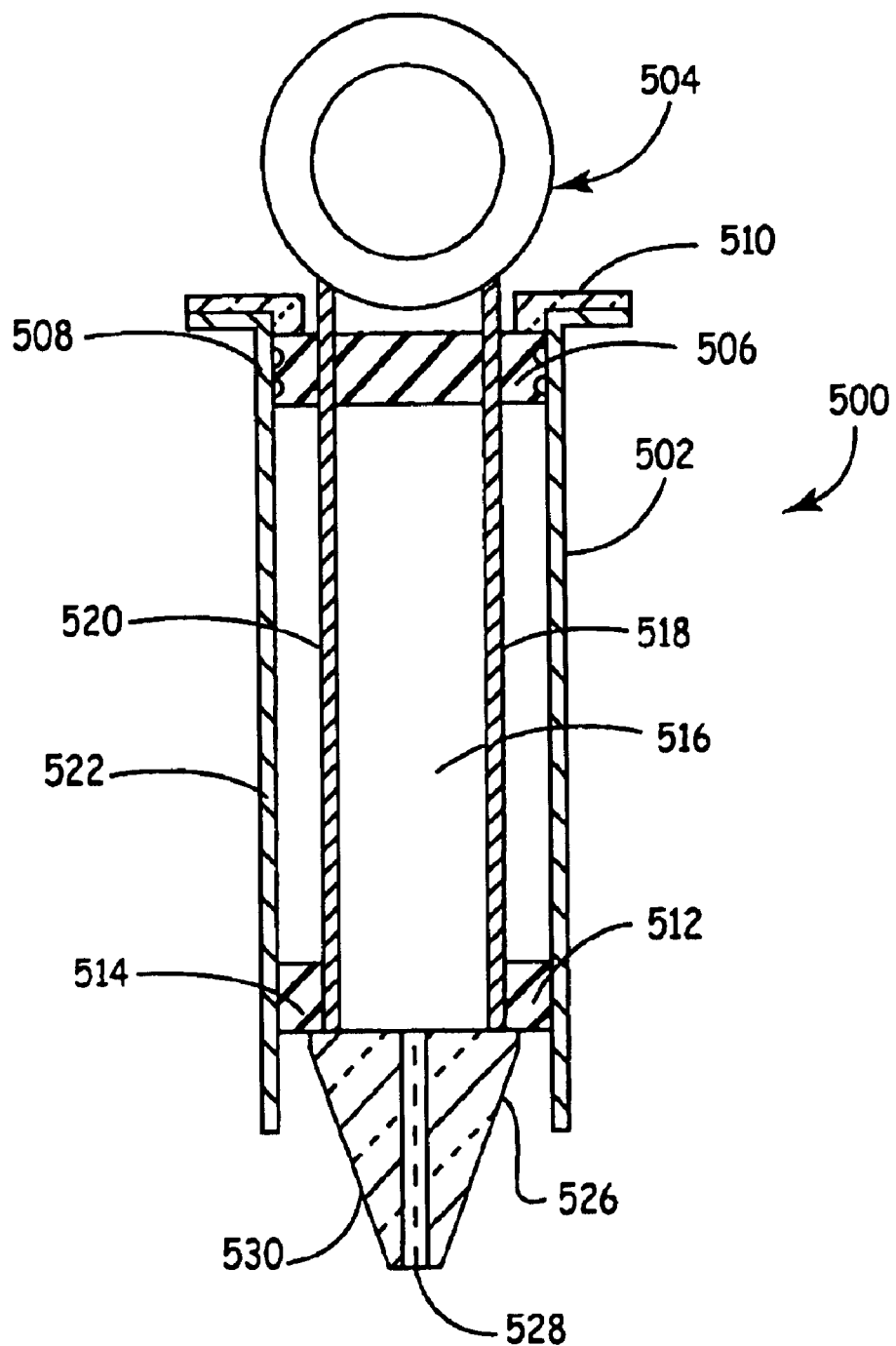
FIG. 10 is a cross-section view of an apparatus in accordance with another preferred embodiment of the invention.

With reference now to FIG. 10, a tissue tract sealing apparatus 500 includes a housing 502, a plunger 504 disposed within the housing 502 and axially moveable therein, a seal 506 disposed at a proximate end 508 of the housing 502 and retained by an end cap 510 and a seal 512 retained to a distal end 514 of the plunger 504 for movement therewith within the housing 502. A volume 516 is defined by an inner surface 518 of the housing 502, the seal 506 and the seal 512.

The plunger includes a first shaft 520 and a second shaft 522 disposed between a grip 524 and a hub 526. The shafts 520 and 522 sealingly pass through apertures (not depicted) formed in the seal 506 and are axially slidable within the apertures. The hub 526 is formed with a passage 528 that is in communication with the volume 516 with the seal 512 forming a seal between the passage and the volume 516. The hub 526 may be formed with a taper 530, or other suitable arrangement, for connecting the apparatus to cannula or similar tube-like member.

As will be appreciated, as the plunger 504 is withdrawn axially from the housing 502, the seal 512 is drawn toward the seal 506 reducing the volume 516. A material 42, such as a procoagulant, disposed within the volume 516 is thereby expelled from the volume 516 through the passage 528.

Figure 11:
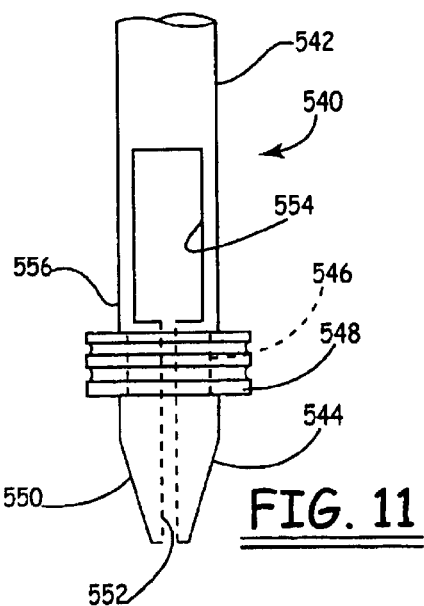
FIG. 11 is a partial view of a plunger that may be used with the apparatus according to various preferred embodiments of the invention.

In FIG. 11, a plunger 540 that may be adapted for use with the apparatus of the present invention includes a shaft 542 disposed between a grip (not depicted) and a hub 544. A recess 546 is formed at a distal end 556 of the shaft 542 for retaining a seal 548 to the distal end 554. The hub 544 may be formed with a taper 550, or other suitable fitting, for connecting the plunger 540 to a cannula or similar tube-like member. The hub 544 is also formed with a passage 552 that is in communication with a chamber 554 formed in the shaft 542.

In use, and according to the present invention, the plunger 540 would be disposed within a housing. The chamber 554 is in communication with a volume defined by the housing and the seal 548 and a seal disposed within the housing at a proximate end thereof. The chamber 554 is adapted to facilitate the flow of material from the volume into the passage 552 in order to reduce the force required to withdraw the plunger from the housing.

Referring to FIG. 12, an apparatus 600 includes a housing 602, a plunger 604 disposed within the housing and axially slidable therein. A seal 606 is disposed about a shaft 608 of the plunger 604 at a proximate end 610 of the housing 602 and is suitably retained at the proximate end 610. A seal 612 is retained to a distal end 614 of the shaft 608 for axial movement with the plunger 604. The plunger 604 includes a hub 615 for connecting the plunger 604 to a cannula or other tube-like member. The plunger 604 further includes a passage (not depicted) formed within the hub 615 in communication with a volume 616 defined by the housing 602.

The apparatus 600 includes an automatic deployment mechanism 618. The automatic deployment mechanism includes a flange 620 formed at a proximate end 622 of the shaft 608. The flange 620 includes a catch 624 that engages a latch 626 that is secured to an exterior wall 628 of the housing 602. The latch 626 includes a button 630 for actuating the apparatus 600. A flange 632 is also formed at a location along the exterior wall 628 and a spring 634 is disposed between the flange 632 and the flange 620 for imparting an axial force on the plunger 604. The axial force is resisted by the engagement of the catch 624 with the latch 626. As shown, the latch 626 extends from the flange 632, although numerous locking arrangements may be used with the device. Also, a wall 636 is secured to the flange 632 covering the spring 634.

In use, the apparatus 600 is secured to a cannula or tube-like member by engagement of the hub 615 with the cannula. At the appropriate moment, the medical professional "pins" the apparatus in relationship to the patient by suitably gripping the housing 602. Next, the medical professional presses the button 630 to release the latch 626 from the catch 624. The spring 634, imparting an axial force between the flange 620 and the flange 632, causes axial translation of the plunger 604. Likewise, the seal 612 is axially translated towards the seal 606 reducing the volume 616 and expelling material disposed within the volume 616 through the passage formed in the hub 615.

Figure 14:
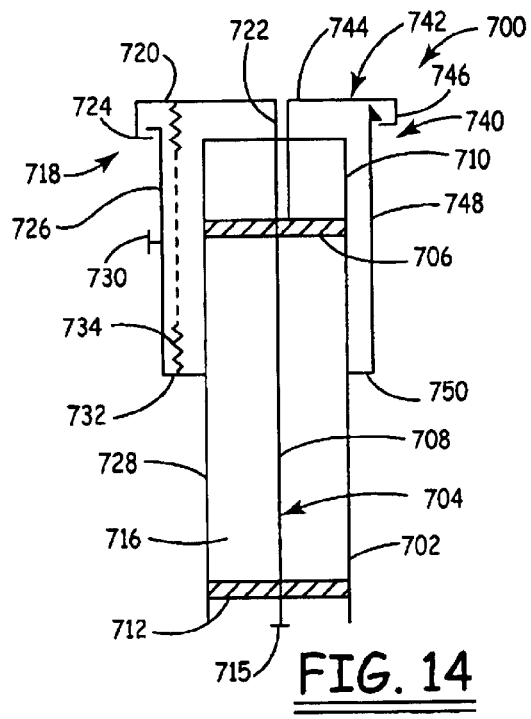
FIG. 14 is a schematic representation of the apparatus illustrated in FIG. 13 in a second configuration.
Figure 15:
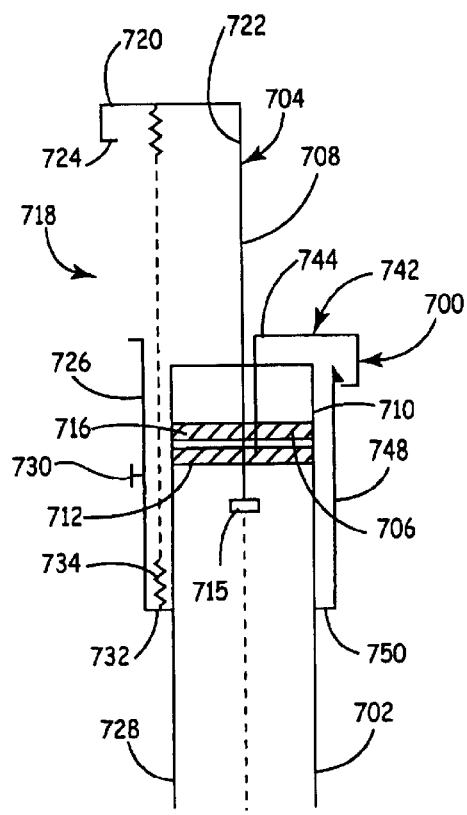
FIG. 15 is a schematic representation of the apparatus illustrated in FIG. 13 in a third configuration.

Referring to FIGS. 13–15, an apparatus 700 includes a housing 702 and a plunger 704 disposed within the housing and axially slidable therein. A seal 706 is disposed about a shaft 708 of the plunger 704 at a proximate end 710 of the housing 702 and is suitably retained at the proximate end 710. A seal 712 is retained to a distal end 714 of the shaft 708 for axial movement with the plunger 704. The plunger 704 includes a hub 715 for connecting the plunger 704 to a cannula or other tube-like member. The plunger 704 further includes a passage (not depicted) formed within the hub 715 in communication with a volume 716 defined by the housing 702.

The apparatus 700 includes an automatic deployment mechanism 718. The automatic deployment mechanism includes a flange 720 formed at a proximate end 722 of the shaft 708. The flange 720 includes a catch 724 that engages a latch 726 that is secured to an exterior wall 728 of the housing 702. The latch 726 includes a button 730 for actuating the apparatus 700. A flange 732 is also formed at a location along the exterior wall 728 and a spring 734 is disposed between the flange 732 and the flange 720 for imparting an axial force on the plunger 704. The axial force is resisted by the engagement of the catch 724 with the latch 726. As shown, the latch 726 extends from the flange 732, although numerous locking arrangements may be used.

The apparatus 700 also includes a priming mechanism 740. The priming mechanism 740 includes a plunger 742 disposed at the proximate end 710 of the housing 702 engaging the seal 706. The plunger 742 is axially moveable with respect to the housing 702. The plunger is formed to include a flange 744 that includes a catch 746. A latch 748 is secured on the exterior wall 728 of the housing 702 and is arranged to engage the catch 746. The latch 748 is shown extending from a flange 750 formed on the exterior wall 728. As will be appreciated, the flange 732 may be extended substantially entirely around the housing 702, or as shown a separate flange 750 maybe formed.

In use, the apparatus 700 is secured to a cannula or tube-like member by engagement of the hub 715 with a cannula. The medical professional advances the plunger 742 distally, thereby advancing the seal 706 within the housing 702. This causes a reduction in the volume 716, which in turn, causes material to be expelled via the passage formed in the hub 715 priming the cannula. The plunger 742 is advanced until the catch 746 engages the latch 748, which retains the plunger 742, and hence, retains the seal 706 in place at the proximate end 710 of the housing 712 as shown in FIG. 14.

At the appropriate moment, the medical professional "pins" the apparatus in relationship to the patient by suitably gripping the housing 702. Next, the medical professional presses the button 730 to release the latch 726 from the catch 724. The spring 734, imparting an axial force between the flange 720 and the flange 732, causes axial translation of the plunger 704. Likewise, the seal 712 is axially translated towards the seal 706 reducing the volume 716 and expelling material disposed within the volume 716 through the passage formed in the hub 715 concomitant with the withdrawal of the cannula (illustrated in phantom) from the patient as shown in FIG. 15.

Figure 16:
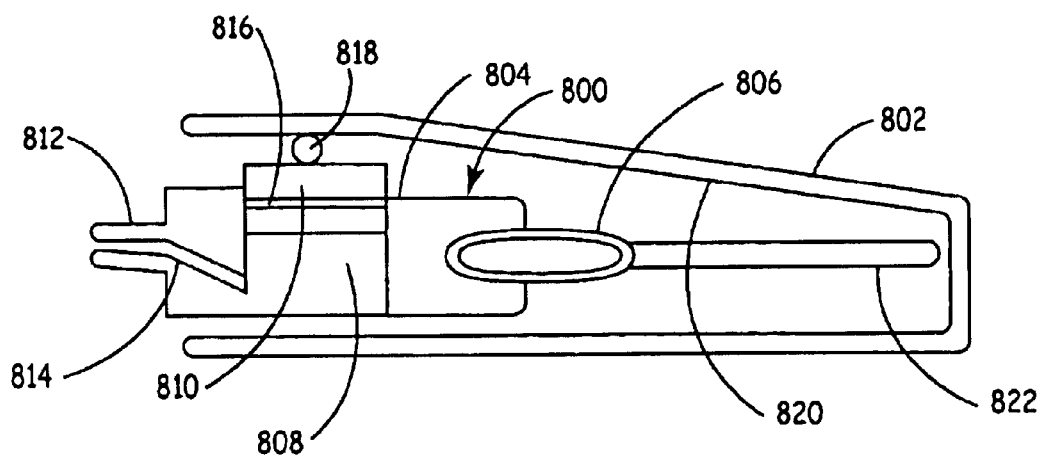
FIG. 16 is a cross-sectional view of an alternate embodiment of the apparatus.

Referring to FIG. 16, another embodiment of the invention is shown. This embodiment generally includes a cannula retractor 800 and a housing 802. Cannula retractor 800 includes body 804 and handgrip 806. Body 804 defines cylinder 808 adapted to receive piston 810. Body 804 further includes cannula holder 812. Lumen 814 is defined through cannula holder 812 and communicates with cylinder 808. Piston 810 includes O-ring 816 and slider 818. Body 804 includes ramp 820 and slot 822.

Figure 17:
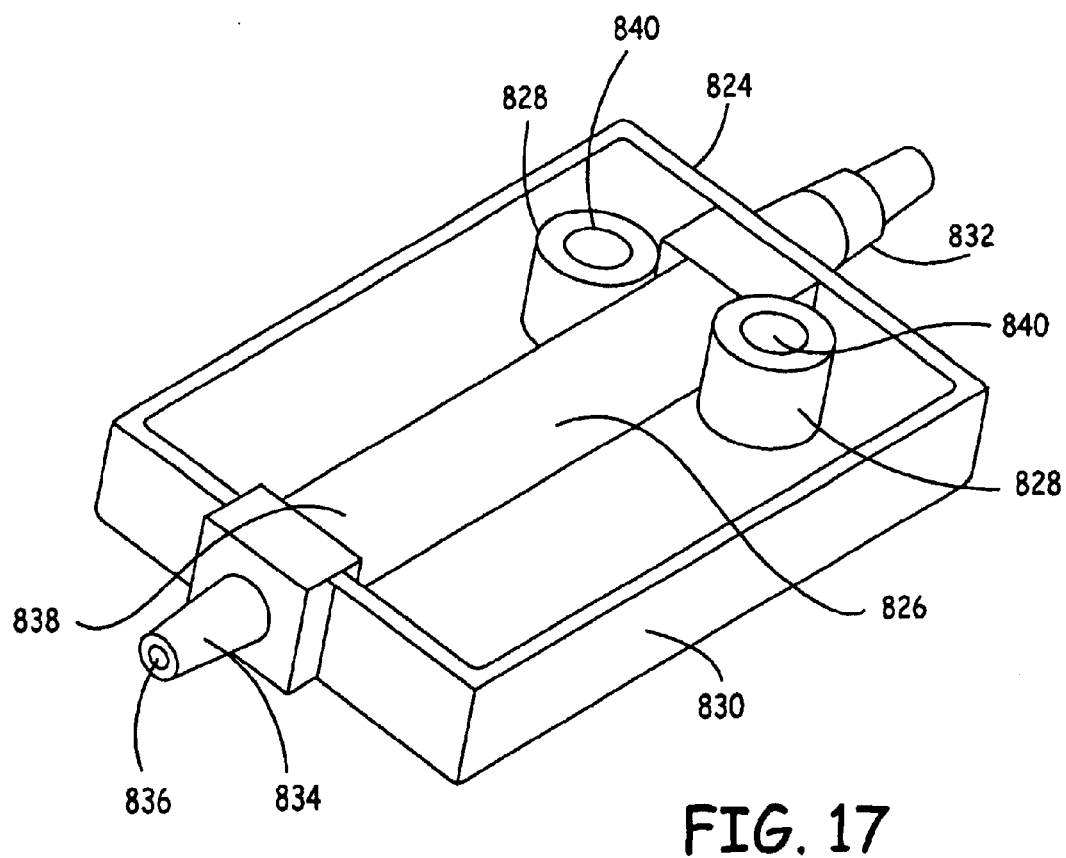
FIG. 17 is a perspective of the embodiment shown in FIG. 16.
Figure 18:
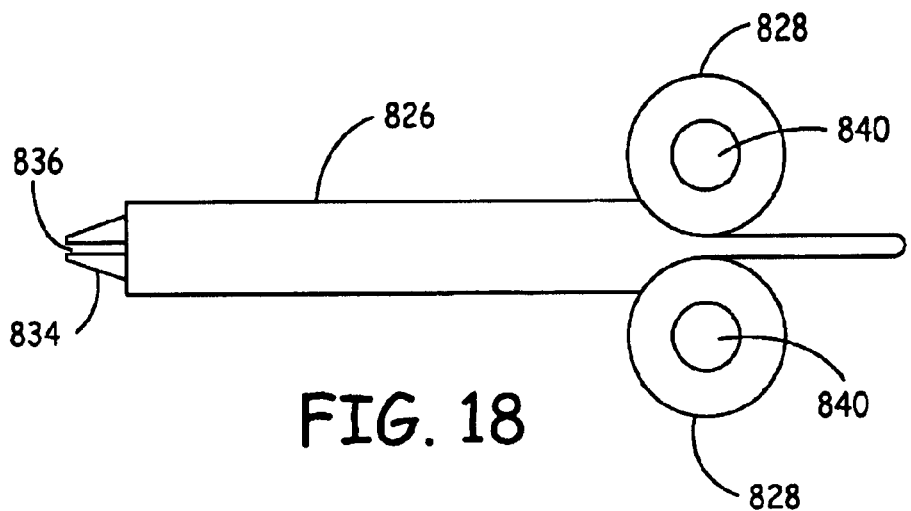
FIG. 18 is a cut-away side view of the embodiment shown in FIG. 16.

Referring to FIG. 17, another embodiment of the present invention generally includes housing 824, compressible reservoir 826 and rollers 828. Housing 824 includes hand grip 830, fill valve 832 and cannula holder 834. Cannula holder 834 defines lumen 836 which is in fluid communication with the interior 838 of compressible reservoir 826. Rollers 828 are supported on roller axles 840. Referring to FIG. 18, rollers 828 are spaced appropriately as compressible reservoir 826 as it is slidably drawn between them.

Figure 19:
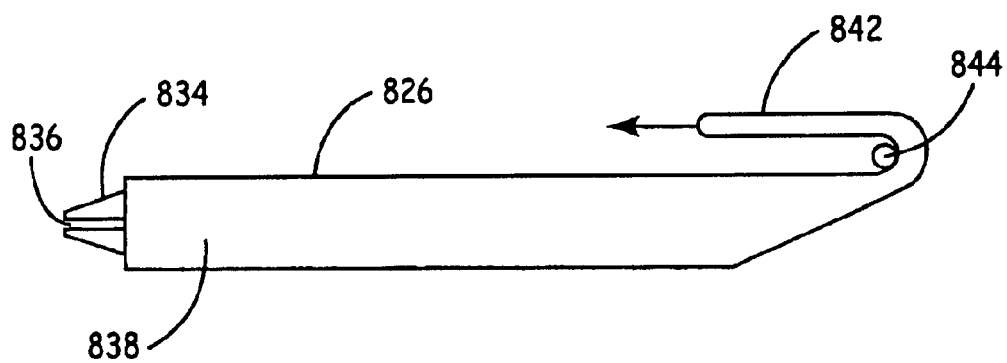
FIGS. 19 and 20 are side views alternate versions of FIG. 18.

Referring to FIG. 19, another embodiment of the present invention is depicted. This embodiment includes compressible reservoir 826, cannula holder 834, reservoir tale 842 and pin 844. Reservoir 826 defines interior 838 which is in communication with lumen 836.

Figure 20:
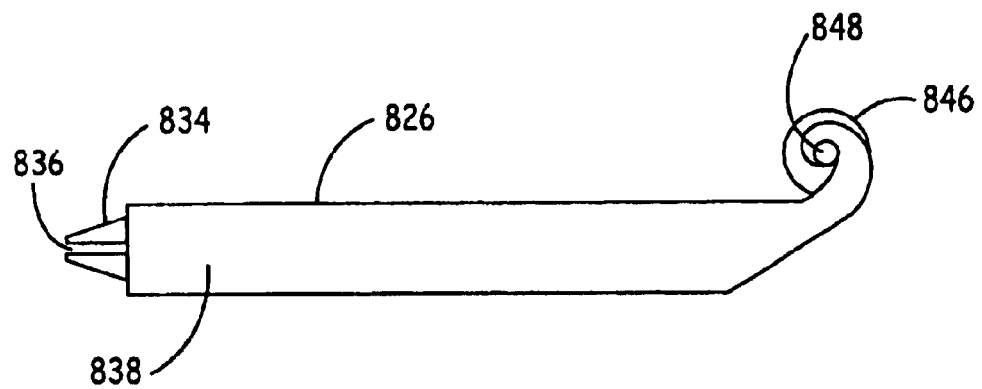
Figure 21:
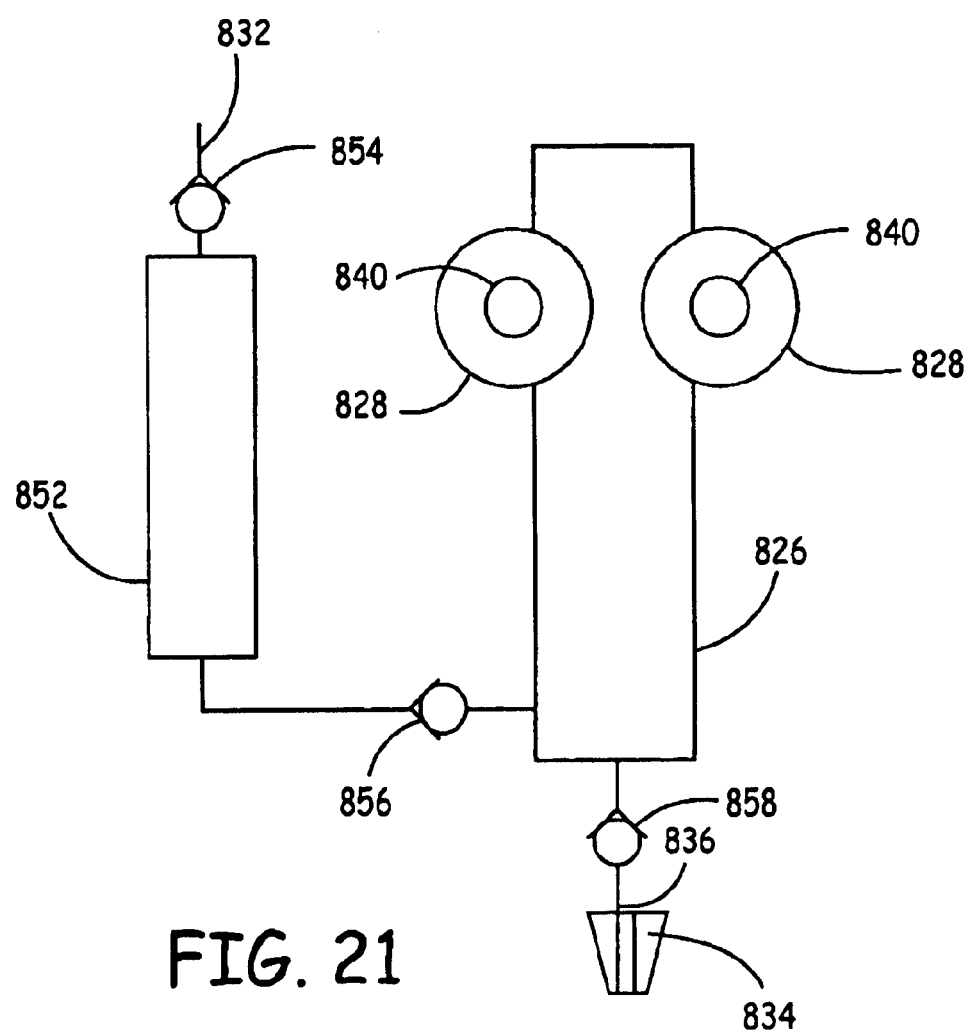
FIG. 21 is a schematic diagram of an automated version of the embodiment of FIG. 16.

Referring to FIG. 20, another embodiment of the compressible reservoir 826 includes cannula holder 834. Reservoir 826 and cannula holder 834 define interior 838 and lumen apex 836. This embodiment further includes windless 846. Windless 846 includes shaft 848 and engagement member 850. Reservoir tale 842 is secured to shaft 848. Engagement member 850 is operably connected to the cannula (not shown). Referring to FIG. 21, an additional embodiment of the invention is shown in schematic. This embodiment is similar to the invention depicted in FIG. 17, with the addition of a secondary reservoir 852, a first check valve 854, a second check valve 856, and third check valve 858. First check valve 854 is connected between fill valve 832 and secondary reservoir 852. Second check valve 856 is in fluid communication between secondary reservoir 852 and reservoir 826. Third check valve 858 is in fluid communication between reservoir 826 and cannula holder 834.

Figure 22:
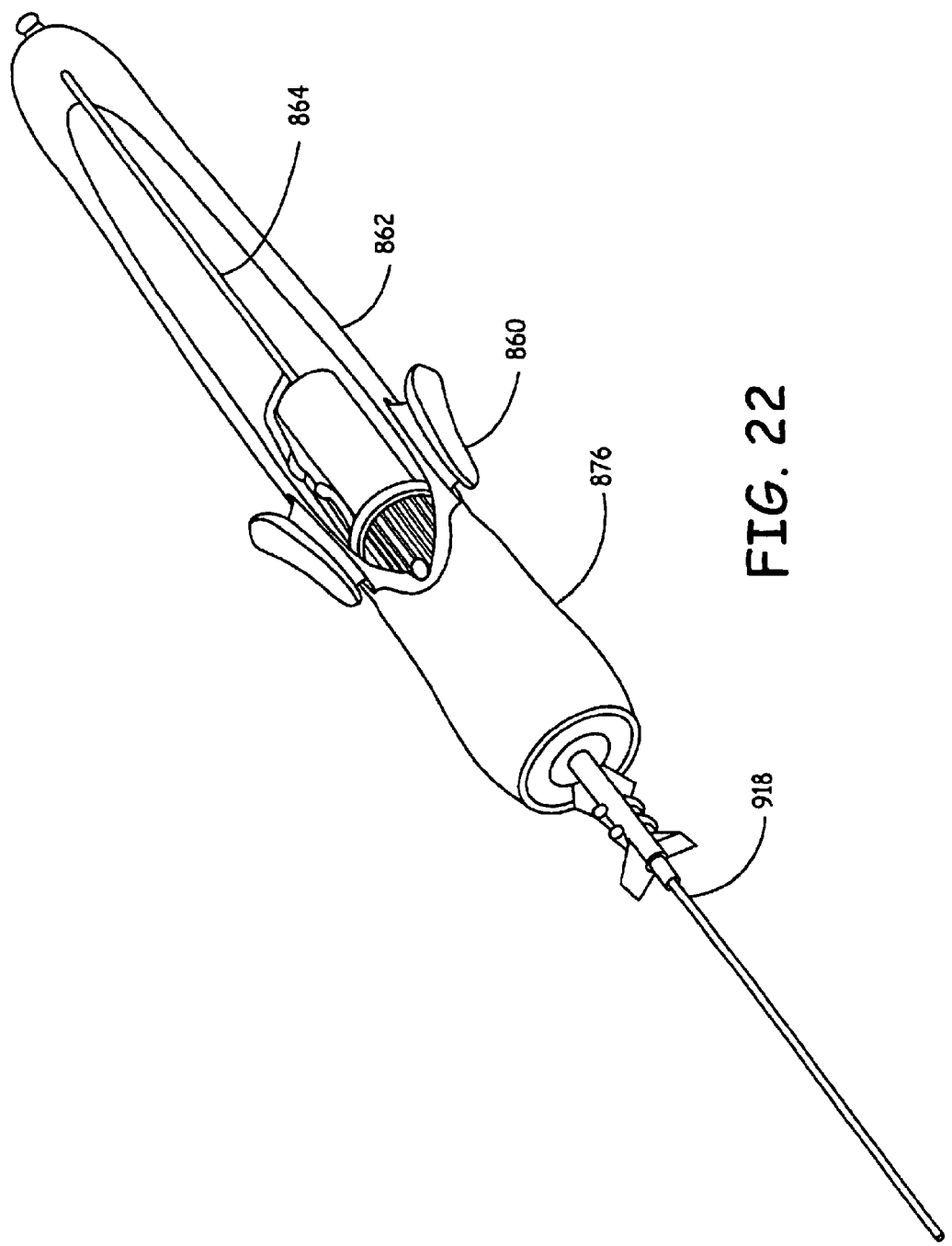
FIG. 22 is a perspective view of another embodiment of the invention.

Referring to FIG. 22, another embodiment of the present invention generally includes cannula retractor 860, barrel housing 862, and piston assembly 864. Piston assembly 864 is affixed to barrel housing 862 at a proximal end thereof. Cannula retractor 860 is slidably movable within barrel housing 862. Piston assembly 864 is received into cannula retractor 860 at a proximal end thereof, and while fixed with relation to barrel housing 862 cannula retractor 864 slides thereover.

Figures 23, 24:
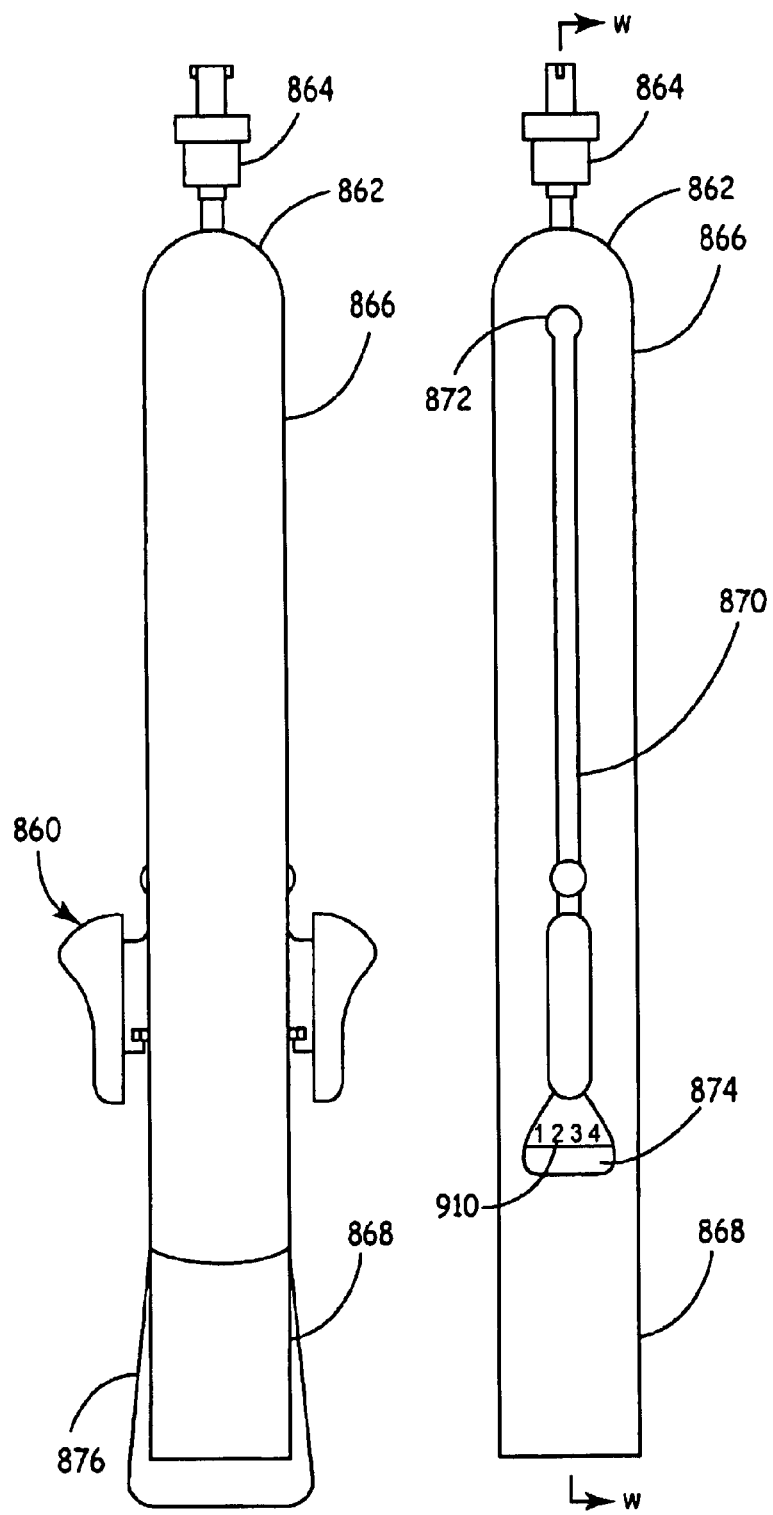
FIG. 23 is a front plan view of the embodiment of FIG. 22.
FIG. 24 is a side plan view of the embodiment of FIG. 22.

Referring to FIGS. 23 and 24, barrel housing 862 is generally cylindrical in shape and has a closed proximal end 866 and an open distal end 868. Barrel housing 862 further defines slot 870, running parallel to the length thereof, slot keyhole 872 and window 874. Referring to FIG. 23, in some embodiments barrel housing 862 includes cover 876 at the distal end 868. Cover 876 may be adapted to extend longitudinally from distal end 868. This extension may be accomplished by a twisting motion at the same time as the extension occurs.

Referring to FIGS. 25 through 33 cannula retractor 860 generally includes reservoir 878 adapted to receive flowable biocompatible substance 879, finger grip assembly 880, connector assembly 882, and primer adjuster 884.

Reservoir 878 generally includes elastomeric tube 886, proximal plug 888 and distal plug 890. Proximal plug 888 defines bore 892 therethrough. Proximal plug 888 is secured to finger grip assembly 880. Finger grip assembly 880 generally includes finger grips 894, compression pads 896, reed springs 898 and end cap 900. Finger grips 894 are preferably shaped for comfortable grasping. Compression pads 896 are adapted to conform to the exterior of elastomeric tube 886. Reed springs 898 are preferably integrally molded and interconnect end cap 900 with finger grips 894. Finger grips 894 further support slot followers 902. Reed spring 898 preferably supports studs 904. Studs 904 are sized and adapted to be received into slot keyhole 872. Finger grips 894 also support cam followers 906.

Primer adjuster 884 includes cylindrical dial 908 bearing indicia 910, grip 912, opposed eccentric cam 914 and detents 916. Cylindrical dial 908 and indicia 910 are adapted to be visible and accessible via window 874. Opposed eccentric cam 914 is adapted to receive cam followers 906. Distal plug 890 may be integral with connector assembly 882.

Connector assembly 882 is connected to distal plug 890 and is adapted to be connected to cannula 918 via a threaded adapter 920. Connector assembly 882 defines bore 922 therethrough which is adapted to be in fluid communication with lumen 924 of cannula 918 and reservoir 878.

Figure 34:
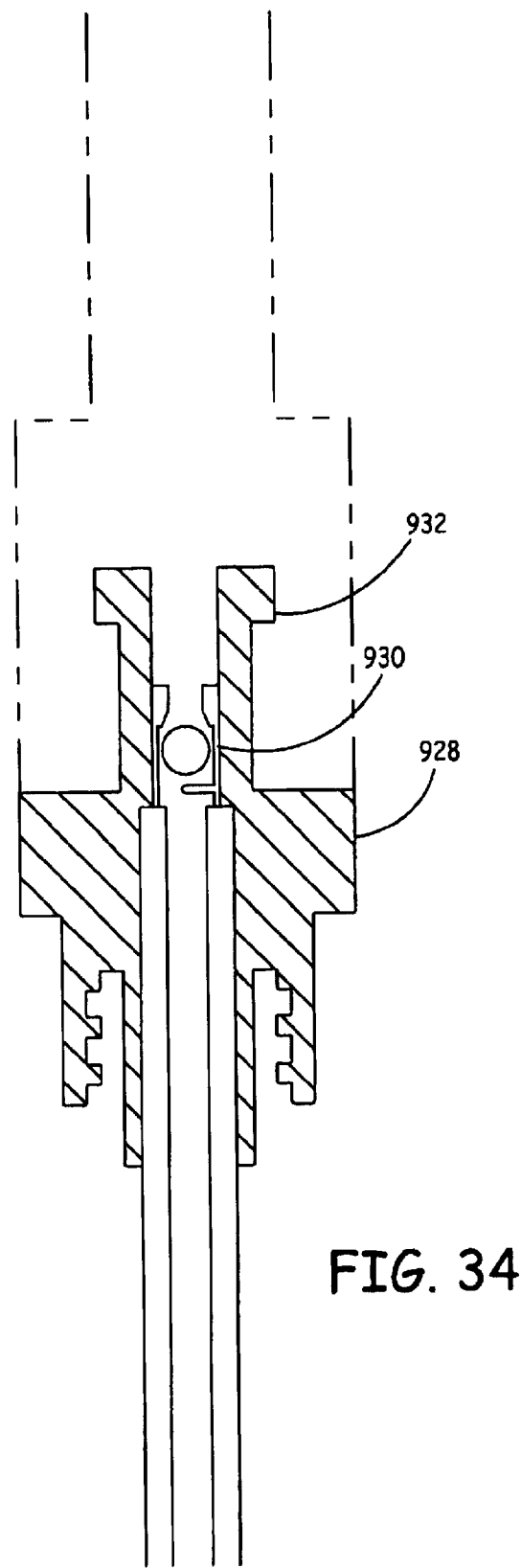
FIG. 34 is a detailed sectional view of a coupling and check valve in accordance with the present invention.

Piston assembly 864 includes tubular member 926 and coupling 928. Tubular member 926 is preferably a rigid stainless steel tube sized to be received into bore 892 in proximal plug 888. Other piston assemblies may be utilized. Coupling 928 is affixed to barrel housing 862 at proximal end 866 thereof. Preferably, coupling 928 is affixed inside of barrel housing 862 at proximal end 866 of barrel housing 862. Referring to FIG. 34, coupling 928 further includes check valve 930 and loading access 932. Check valve 930 is adapted so as to allow inflow into tubular member 926. Loading access 932 is accessible from outside of proximal end 866 of barrel housing 862 and is adapted to allow the filling of reservoir 878.

In operation, referring to FIG. 16, in this embodiment of the tissue tract sealing device, cylinder 808 is filled with a flowable biocompatible substance. When it is desired to retract the cannula, the operator of the tissue tract sealing device grasps the housing 802 with one hand to hold it in place and grasps handgrip 806 with the other hand. Handgrip 806 is pulled away from the tissue in order to retract the cannula. As handgrip 806 is retracted, slider 818 proceeds down a ramp 820. As slider 818 travels down ramp 820, piston 810 is pressed into cylinder 808. As piston 810 is pressed into cylinder 808, the flowable therapeutic substance is discharged from the cylinder via lumen 814 and through the cannula to fill the tissue tract. Size of piston 810 and cylinder 808 can be varied according to the desired amount of therapeutic substance to be applied. Further, the slope of ramp 820 can be varied in order to adjust the discharge of the therapeutic substance. This embodiment of the tissue tract sealing device can be adapted to have a primer function. A primer function pre-fills a cannula with therapeutic substance so that as soon as the cannula retraction begins, the therapeutic substance is discharged from the end of the cannula. This is readily done by placing a step (not shown) in ramp 820 to provide an initial discharge of therapeutic substance sufficient to fill the length of the cannula.

Referring to FIG. 17, compressible reservoir 826 can be filled with a therapeutic substance via fill valve 832. Once compressible reservoir 826 is filled with therapeutic substance, the cannula may be primed with therapeutic substance by slidably moving rollers 828 towards one another a sufficient distance to discharge a sufficient amount of the therapeutic substance to fill the cannula.

When it is desired to withdraw the cannula and seal the tissue tract, the surgeon grasps hand grip 830 with one hand and cannula holder 836 with the other hand. As the cannula is withdrawn, rollers 828 remain in a fixed position relative to the tissue in which the cannula is inserted. Compressible reservoir 826 then travels longitudinally relative to rollers 828. As it does so, the peristaltic action of rollers 828 squeezing compressible reservoir 826 discharges the therapeutic substance via lumen 836 and into the cannula (not shown) so as to fill the tissue tract.

FIG. 18 schematically depicts the interaction of rollers 828 with compressible reservoir 826 as the cannula is withdrawn.

Referring to FIG. 19, in another embodiment of the tissue tract sealing device, as the cannula is withdrawn, reservoir tale 842 is pulled forward so that flexible compressible reservoir 826 is drawn over pin 844. This action squeezes reservoir 826 so as to discharge a desired quantity of the therapeutic substance as the cannula is withdrawn.

Referring to FIG. 20, in this embodiment of the invention, reservoir tale 842 is secured to windless 846 via shaft 848. In this embodiment, the tissue tract sealing device is adapted so that as the cannula is withdrawn, windless 846 is turned, winding the reservoir tale 842 onto shaft 848. Thus, as the cannula is withdrawn, compressible reservoir 826 is rolled, much in the manner of a toothpaste tube, in order to discharge a therapeutic substance through lumen 836 and down to cannula (not shown).

Referring to FIG. 21, at another embodiment of the tissue tract sealing device is shown in schematic. This embodiment includes structures depicted in FIG. 17 with the addition of a secondary reservoir 852. In this embodiment, the secondary reservoir 852 is filled with a therapeutic substance via fill valve 832. The therapeutic substance opens first check valve 854. Rollers start at a position near to third check valve 858 are withdrawn to a position distal to check valve 858. As the rollers are withdrawn, second check valve 856 opens and third check valve 858 closes allowing the therapeutic substance to be drawn into compressible reservoir 826. As the cannula is withdrawn, compressible reservoir 826 is drawn between rollers 828 discharging the therapeutic substance through lumen 836 via third check valve 858.

Figure 25:
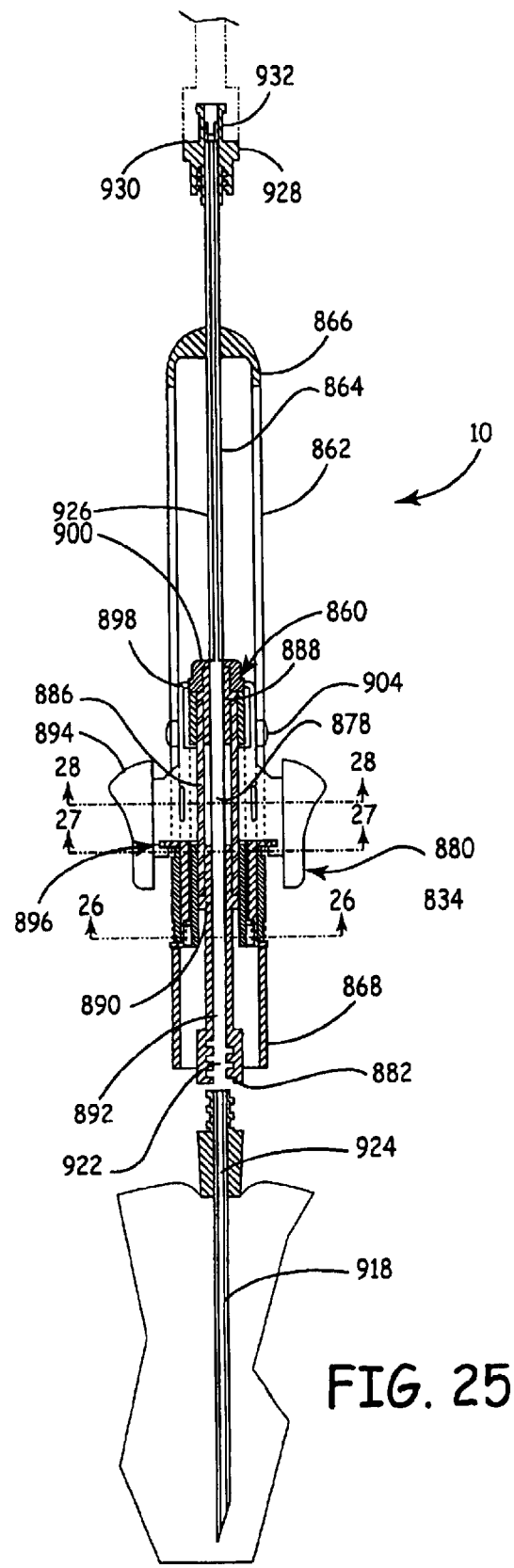
FIG. 25 is a partially exploded sectional view of the embodiment of FIG. 22.
Figure 26:
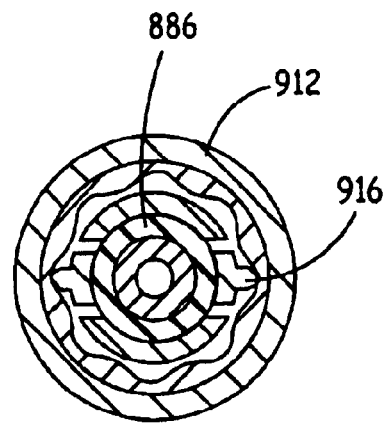
FIG. 26 is a cross-sectional view taken along section line 26—26 of FIG. 25.
Figure 27:
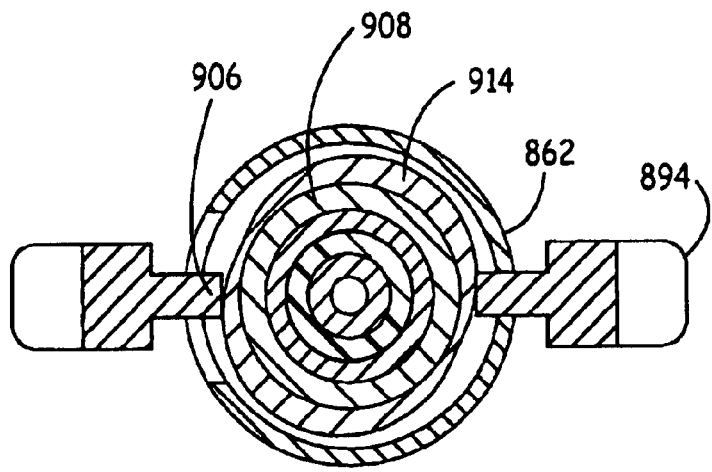
FIG. 27 is a cross-sectional view taken along section line 27—27 of FIG. 25.
Figure 28:
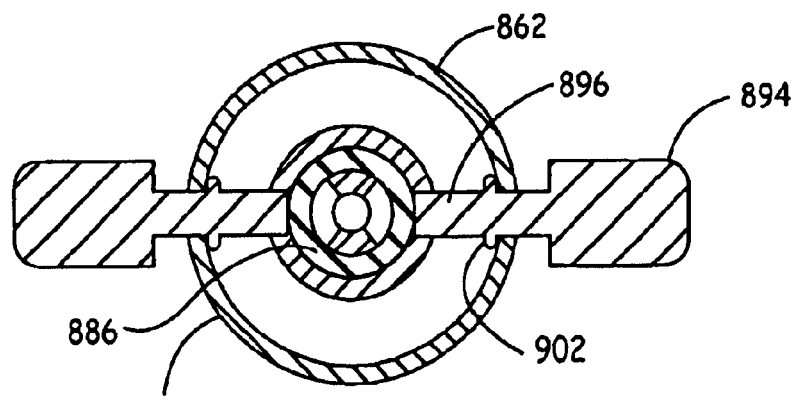
FIG. 28 is a cross-sectional view taken along section line 28—28 of FIG. 25.
Figure 29:
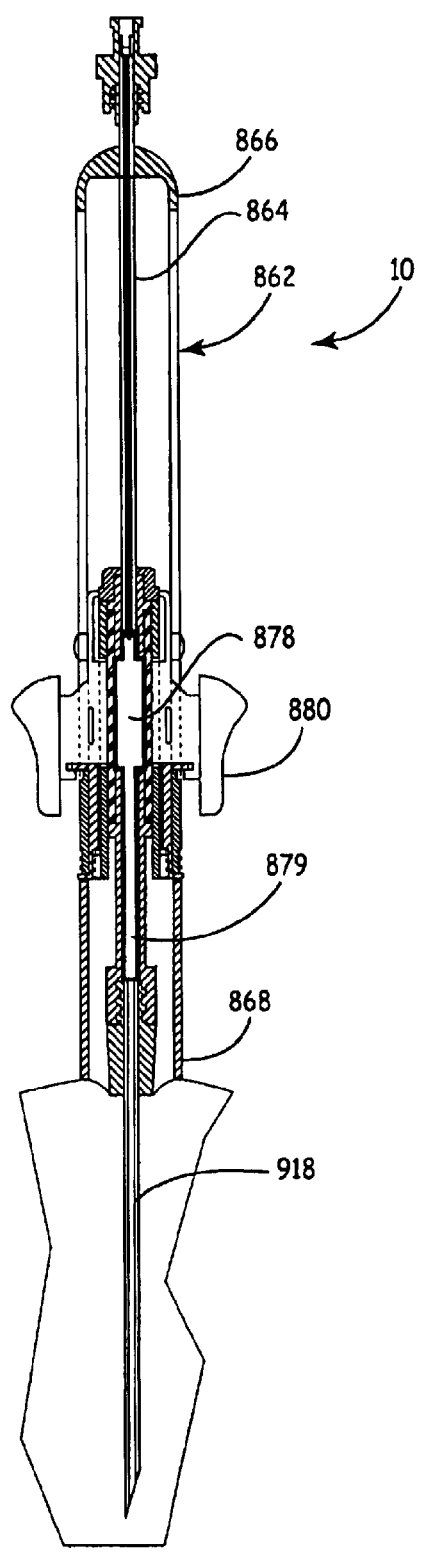
FIG. 29 is a sectional view of the embodiment in situ showing a first step in an operational sequence.
Figure 30:
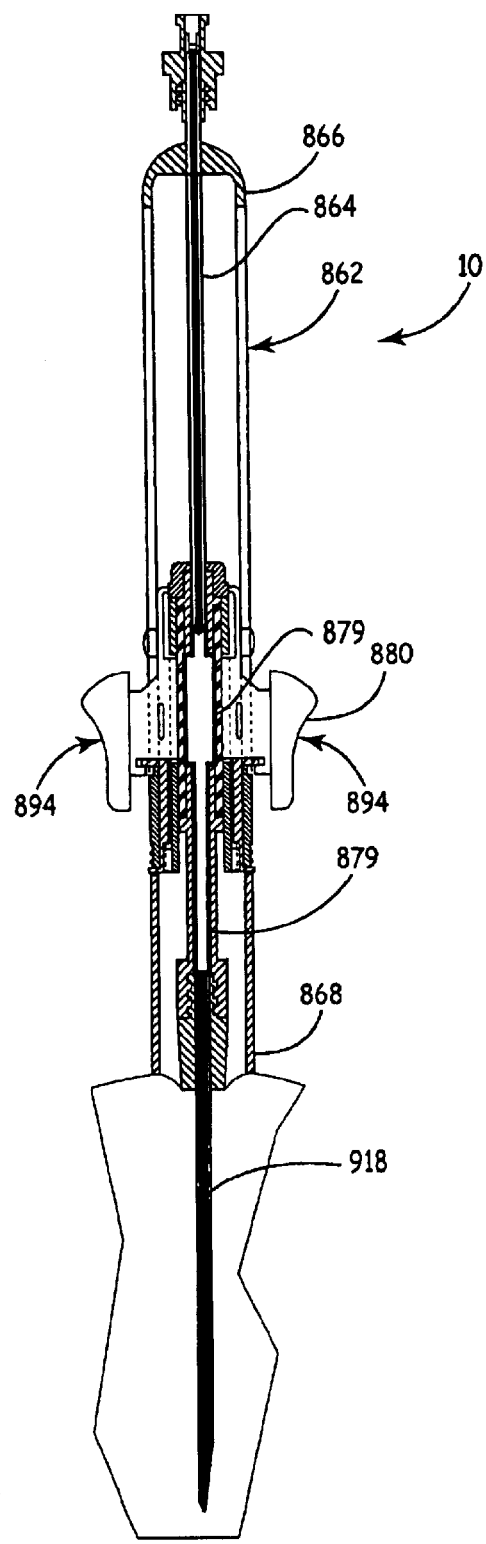
FIG. 30 is a sectional view of the embodiment in situ showing a second step in an operational sequence.
Figure 31:
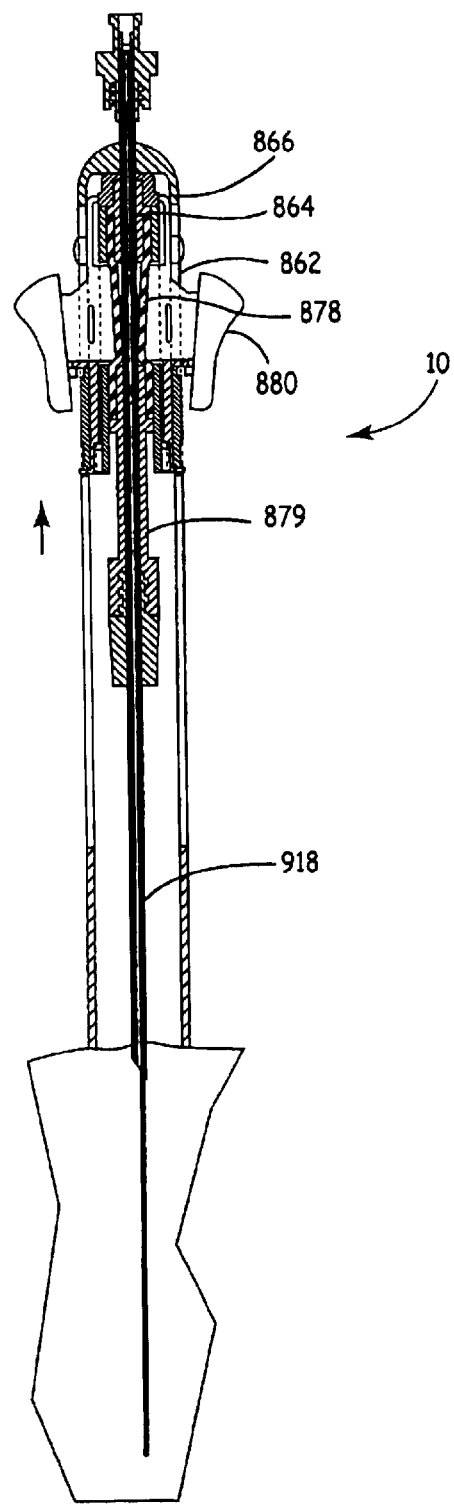
FIG. 31 is a sectional view of the embodiment in situ showing a third step in an operational sequence.
Figure 32:
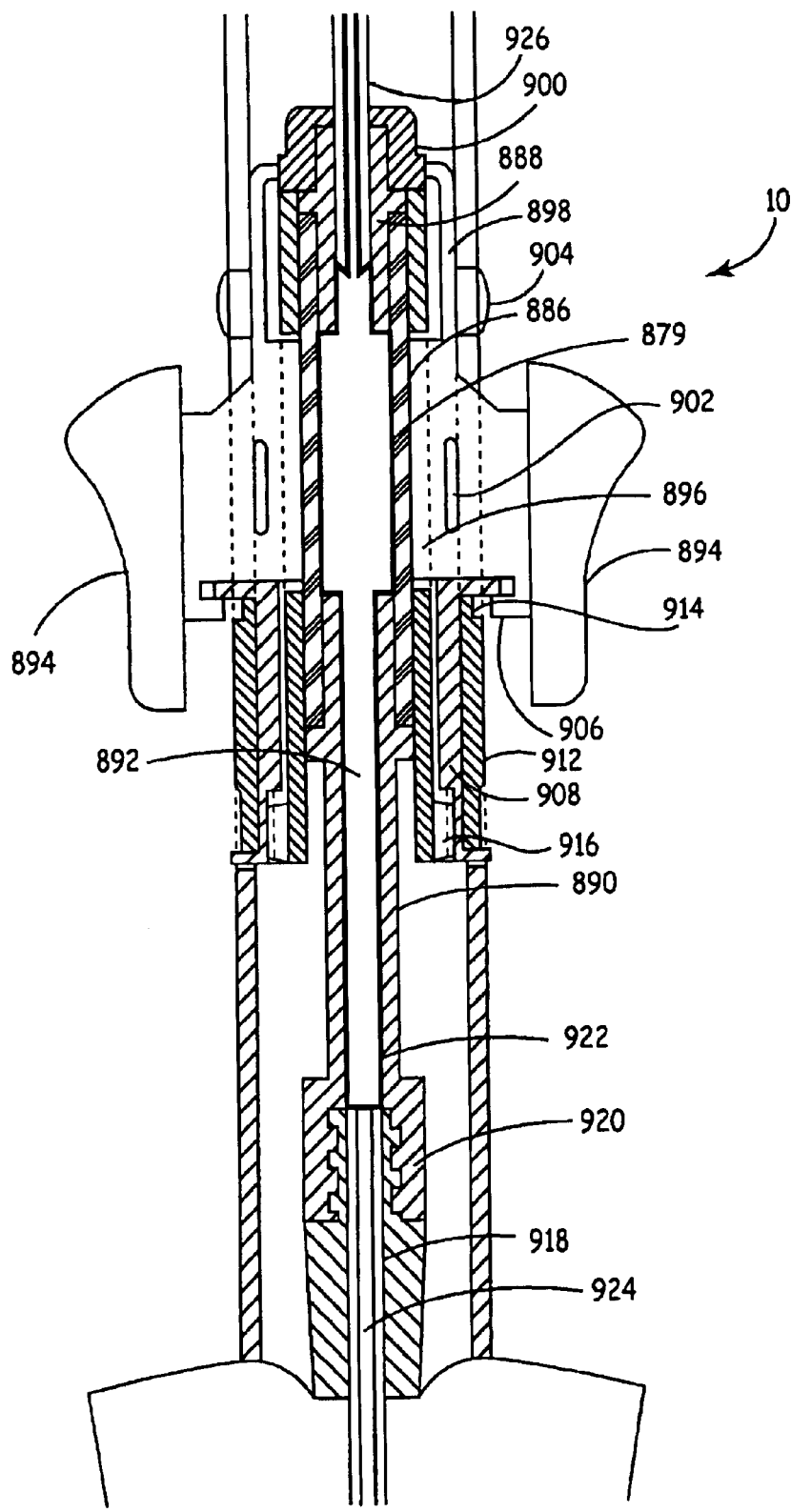
FIG. 32 is a detailed sectional view of FIG. 29.
Figure 33:
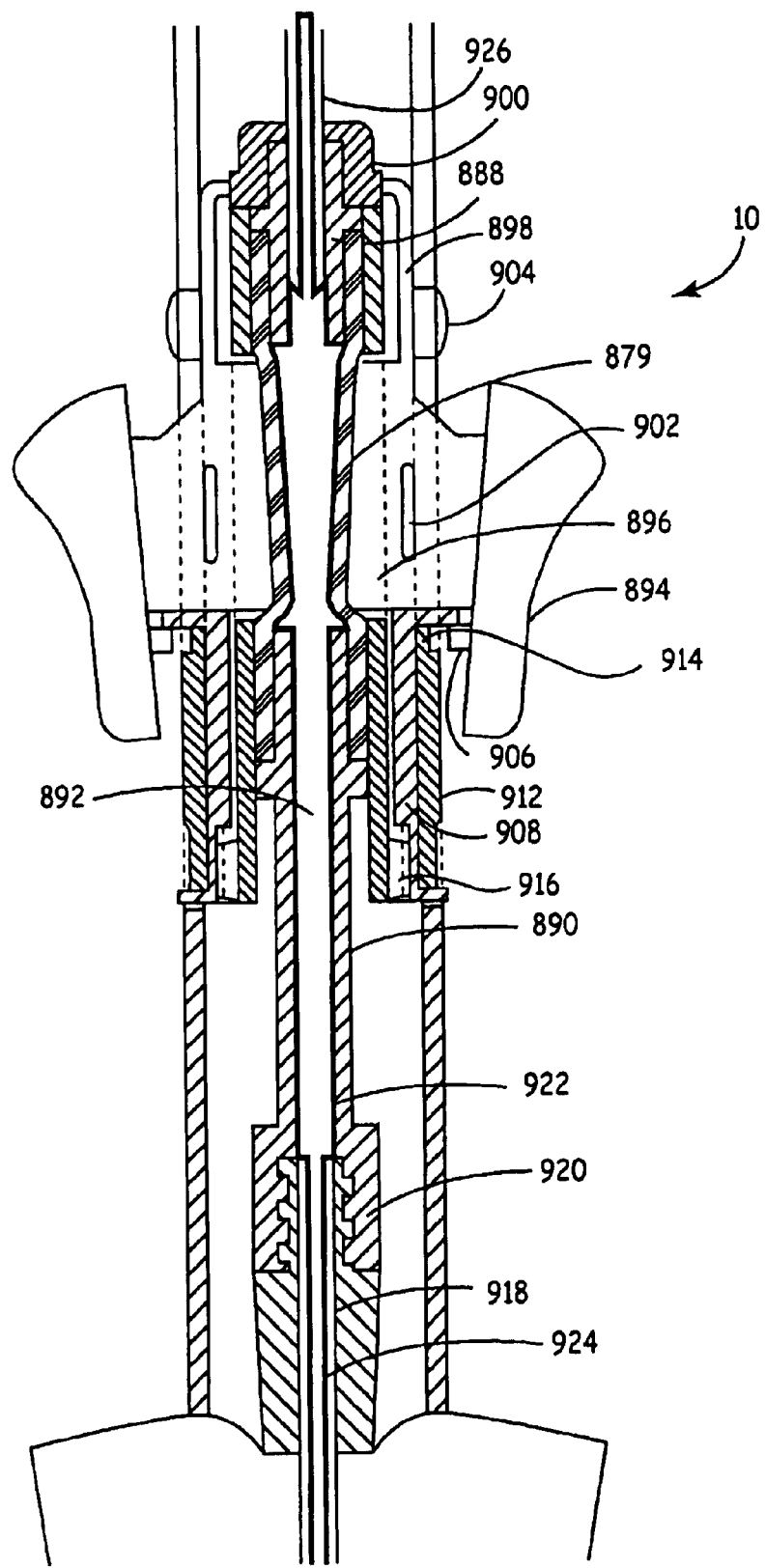
FIG. 33 is a detailed sectional view of FIG. 30.

Referring to FIGS. 29 and 31, an embodiment of the tissue tract sealing device is shown attached to a pre-placed cannula 918. Reservoir 878 is depicted filled with a flowable biocompatible substance 879. Referring to FIGS. 24, 25, and 30, when the operator of the tissue tract sealing device desires to prime the cannula 918 with flowable biocompatible substance 879, the operator first adjusts primer adjuster 884 so that an appropriate indicia 910 is visible through window 874. Indicia 910 is calibrated so as to deliver an appropriate amount of flowable substance 879 to completely fill cannula 918. When it is desired to prime cannula 918, the operator then applies pressure to finger grips 894 as depicted in FIGS. 30 and 32. Note that when pressure is applied to finger grips 894, elastomeric tube 886 is compressed thereby reducing the volume of reservoir 878 forcing flowable substance 879 into cannula 918. Referring to FIG. 33, the operator then pulls finger grips 894 toward proximal end 866 of barrel housing 862. Because piston assembly 864 is affixed to barrel housing 862, and the operator holds barrel housing 862 against the skin of a patient as cannula retractor 860 is moved, flowable substance 879 is discharged into the tissue tract substantially filling at least part of the tissue tract.

While the invention has been described in detail with reference to the preferred embodiment thereof, it will be apparent to one skilled in the art that various changes and modifications can be made and equivalents employed, without departing from the present invention.

What is claimed:

1. A tissue tract sealing device for use with a medical cannula to seal a tissue tract made in a living tissue by the medical cannula with a flowable biocompatible material, the tissue tract sealing device comprising:
    an elongated housing having a coupling on a distal end adapted to fluidly couple the device to the medical cannula;
    a reservoir within the housing that contains the flowable biocompatible material;
    a piston arrangement within the housing and in fluid connection with the reservoir that discharges the flowable biocompatible material from the reservoir to the coupling; and
    a cannula rector operably engaged in at least one longitudinal channel defined along at least a portion of the elongated housing, the cannula retractor operably connected to the coupling and the piston arrangement such that sliding of the cannula retractor along the channel causes the cannula to withdraw from the tissue tract and causes the piston arrangement to discharge the flowable biocompatible material into the tissue tract.

2. The tissue tract sealing device of claim 1, wherein the cannula retractor comprises a pair of opposed finger grip assemblies slidable within a pair of opposed longitudinal channels defined in the elongated housing.

3. The tissue tract sealing device of claim 2, wherein at least one of the finger grip assemblies further includes a priming member that operates to prime the cannula with a predetermined amount of the biocompatible flowable material without longitudinal movement of the finger grip assembly.

4. The tissue tract sealing device of claim 3, further comprising an adjustment mechanism operably connected to the priming member to selectively adjust the predetermined amount of the biocompatible flowable material used to prime the cannula when the priming member is operated.

5. The tissue tract sealing device of claim 3, wherein the priming member comprises a compression member.

6. The tissue tract sealing device of claim 1, further comprising a second coupling at a proximal end of the elongated housing that provides fluid connection to the reservoir for loading the reservoir with the flowable biocompatible material.

* * * * *